(12) United States Patent
Sullivan et al.

(10) Patent No.: US 11,000,662 B2
(45) Date of Patent: May 11, 2021

(54) RESPIRATOR MASK

(71) Applicant: AUSTRALIAN CENTRE FOR ADVANCED MEDICAL TECHNOLOGY PTY LTD, Balmain (AU)

(72) Inventors: Colin Sullivan, Balmain (AU); Peter Spencer, Balmain (AU)

(73) Assignee: AUSTRALIAN CENTRE FOR ADVANCED MEDICAL TECHNOLOGY PTY LTD

( * ) Notice: Subject to any disclaimer, the term of this patent is extended or adjusted under 35 U.S.C. 154(b) by 1138 days.

(21) Appl. No.: 15/130,443

(22) Filed: Apr. 15, 2016

(65) Prior Publication Data

US 2016/0228666 A1 Aug. 11, 2016

Related U.S. Application Data

(63) Continuation of application No. 14/531,679, filed on Nov. 3, 2014, now abandoned, which is a (Continued)

(30) Foreign Application Priority Data

Sep. 28, 2006 (AU) ................. 2006905360

(51) Int. Cl.
*A61M 16/06* (2006.01)
*A61M 16/00* (2006.01)

(52) U.S. Cl.
CPC .... *A61M 16/0683* (2013.01); *A61M 16/0057* (2013.01); *A61M 16/06* (2013.01); *A61M 16/0616* (2014.02); *A61M 16/0633* (2014.02)

(58) Field of Classification Search
CPC .............. A61M 16/06; A61M 16/0605; A61M 16/0616; A61M 16/0622; A61M 16/0627;
(Continued)

(56) References Cited

U.S. PATENT DOCUMENTS 4,907,584 A * 3/1990 McGinnis ............. A61M 16/06
128/206.24
5,937,851 A 8/1999 Serowski et al.
(Continued)

FOREIGN PATENT DOCUMENTS

DE 29723101 U1 5/1998
EP 958841 A2 11/1999
(Continued)

OTHER PUBLICATIONS

International Preliminary Report on Patentability from corresponding International Application No. PCT/AU2007/001455 dated Mar. 31, 2009.
(Continued)

*Primary Examiner* — Margaret M Luarca

(57) ABSTRACT

A mask for supplying gas under pressure to an airway of a human including a flexible manifold shell, an air inlet connected to an air delivery pipe, and at least two side walls which are at least partially formed by portions of the manifold shell. A flexible face contacting element defines an orifice to accommodate the nose of the human. Straps connected to the mask allow forces exerted by the straps to deform the manifold shell at least along X and Y axes, creating a variety of different orifice shapes. The face contacting part includes a flexible membrane allowing X and Y axis movement of the mask and movement of the mask along a Z axis between the user's face and the manifold shell. The flexible membrane may deform while retaining a gas seal against the face of a wearer.

29 Claims, 22 Drawing Sheets

Neutral Position - No Tension Applied to Shape Forming Element

Related U.S. Application Data continuation of application No. 12/443,415, filed as application No. PCT/AU2007/001455 on Sep. 28, 2007, now abandoned.

(58) Field of Classification Search
CPC .......... A61M 16/0644; A61M 16/0633; A61M 16/0683; A61M 2016/0661; A62B 18/084; A62B 18/08
See application file for complete search history.

(56) References Cited

U.S. PATENT DOCUMENTS

| | | | |
|---|---|---|---|
| 6,119,694 A * | 9/2000 | Correa | A61M 16/0666 128/207.13 |
| 6,631,718 B1 | 10/2003 | Lovell | |
| 6,886,564 B2 * | 5/2005 | Sullivan | A61M 16/06 128/206.21 |
| 2004/0035428 A1 | 2/2004 | Olsen et al. | |
| 2005/0150497 A1 | 7/2005 | Eifler et al. | |
| 2005/0199239 A1 * | 9/2005 | Lang | A61M 16/06 128/206.24 |
| 2005/0284477 A1 * | 12/2005 | Schrader | A61M 16/06 128/205.25 |
| 2006/0027236 A1 * | 2/2006 | Barnett | A61M 16/06 128/206.24 |
| 2006/0237018 A1 | 10/2006 | McAuley et al. | |
| 2006/0283457 A1 | 12/2006 | Woodard et al. | |

FOREIGN PATENT DOCUMENTS

| | | | |
|---|---|---|---|
| EP | 1520599 A1 | 4/2005 | |
| EP | 1658873 A1 | 5/2006 | |
| WO | 0132250 A1 | 5/2001 | |
| WO | WO0132250 * | 5/2001 | .......... A61M 16/06 |
| WO | 0197892 A1 | 12/2001 | |
| WO | 0205883 A1 | 1/2002 | |

OTHER PUBLICATIONS

International Search Report and Written Opinion from corresponding International Application No. PCT/AU2007/001455 dated Dec. 17, 2007.

* cited by examiner

Neutral Position - No Tension Applied to Shape Forming Element

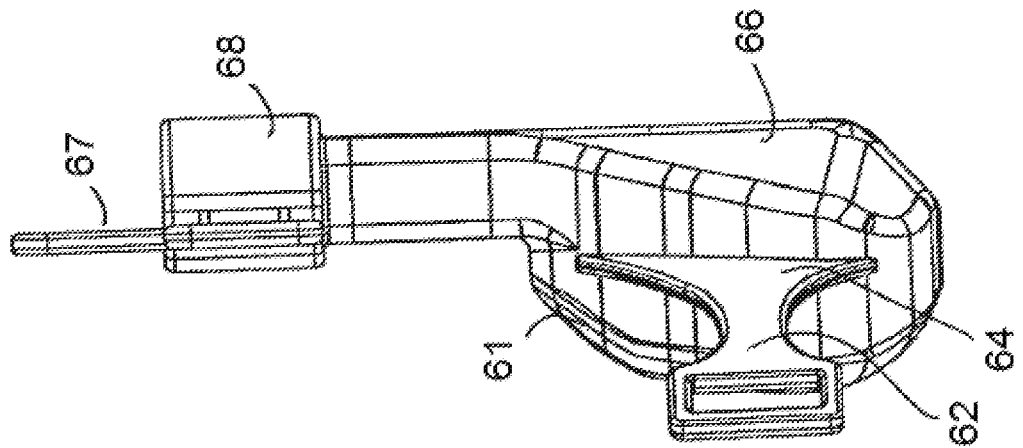
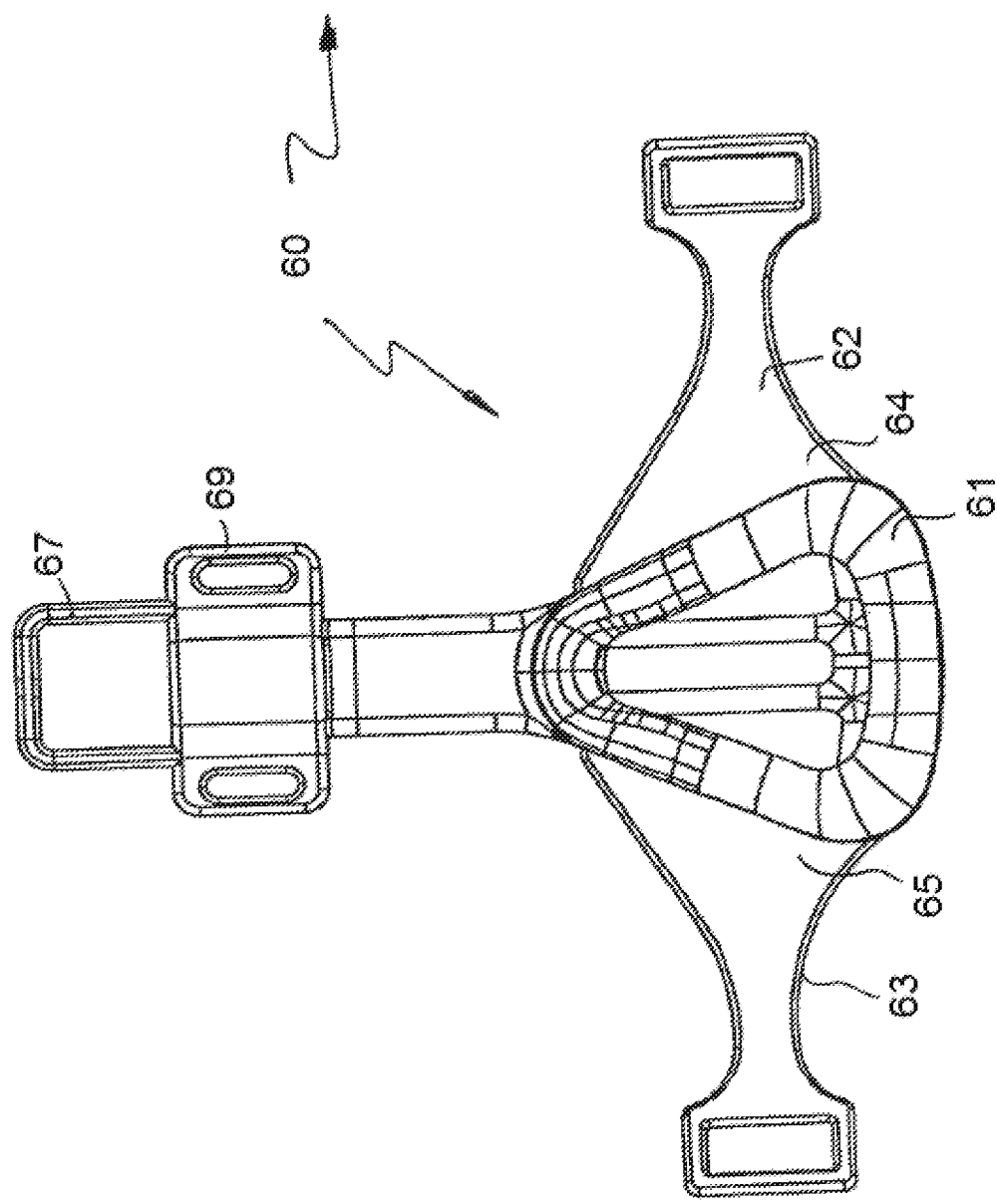
FIG. 13b
FIG. 13a

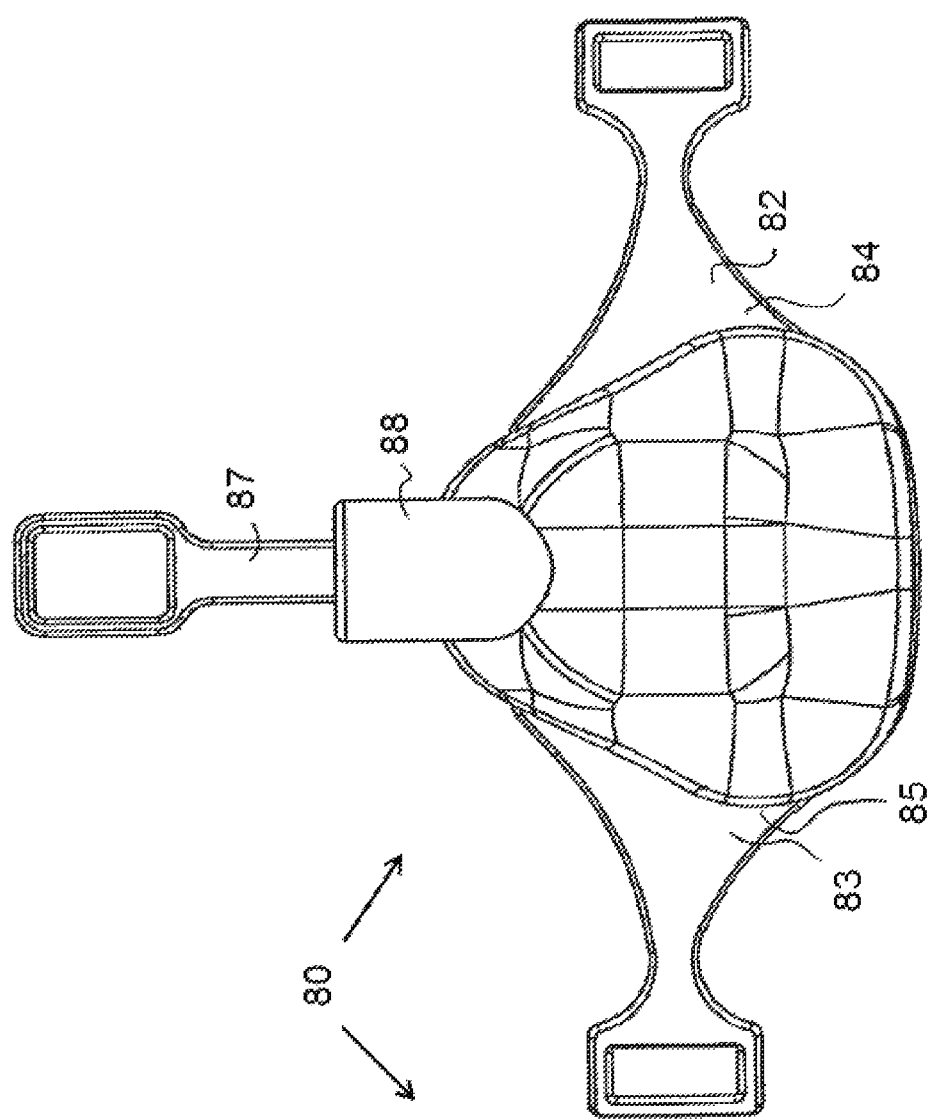
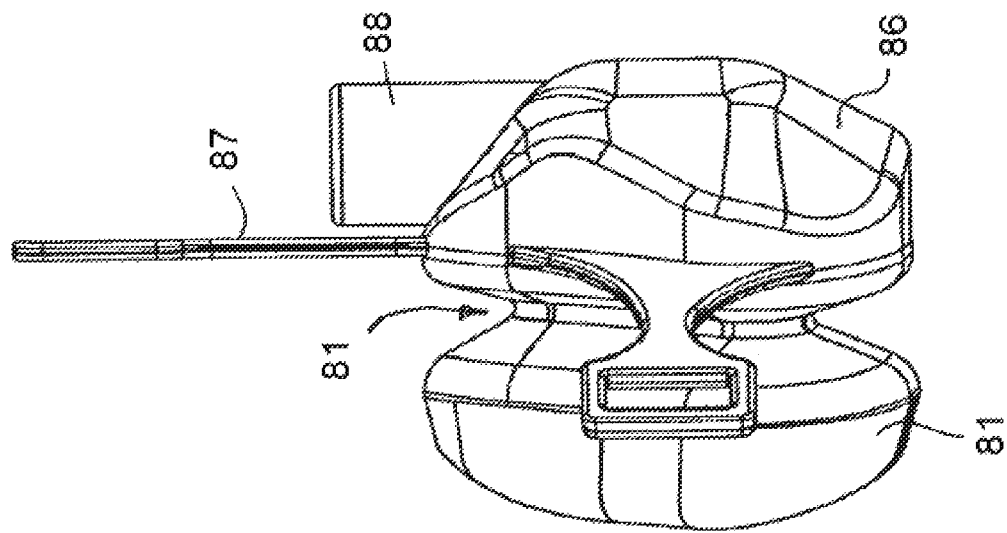
FIG. 17b
FIG. 17a

RESPIRATOR MASK

CROSS-REFERENCE TO RELATED APPLICATIONS

This application is a Continuation of U.S. patent application Ser. No. 14/531,679, titled "IMPROVED RESPIRATOR MASK," filed on Nov. 3, 2014, which is a Continuation of U.S. patent application Ser. No. 12/443,415 titled "RESPIRATOR MASK," filed on Oct. 29, 2009, which is a U.S. national stage application under and claims the benefit of 35 U.S.C. § 371 of International Application No. PCT/AU2007/001455, filed on Sep. 28, 2007, titled "IMPROVED RESPIRATOR MASK," which claims priority to Australian application no. 2006905360, filed on Sep. 28, 2006, titled "IMPROVED RESPIRATOR MASK," each of which is incorporated herein by reference in its entirety.

FIELD OF THE INVENTION

This invention relates to a mask, in particular to a mask for supplying gases, typically air or oxygen, to the airways (nose or no and mouth) of humans. Such masks are often referred to as "respirator masks". Such masks are particularly suited to applying continuous positive airway pressure (CPA) to patients for treatment of sleep apnea, however the invention is not in any way limited to masks for that use only. More particularly the invention relates to a face mask including straps which terminate in webs which engage opposing walls of the mask and which have a contact length which transfers in use loadings applied to the straps through to the mask allowing the mask to displace on a users face in an X, Y or Z direction and without breaking a seal created between a face contacting part of the mask and the mask.

BACKGROUND OF THE INVENTION

In general, conventional respirator masks consist of a face contacting part which defines an orifice and which fits over the patient's nose and/or mouth and provides a gas tight seal against the patient's skin. The reverse side of the orifice is enclosed by a manifold part for the delivery of pressurized gases to the patient's nose and/or mouth via a gas delivery tube connected to the manifold. Typically, the manifold part is made from a rigid material to which an adjustable harness, for retaining the mask on a patient's head, is attached. The geometry of the manifold is fixed. When adjusted and placed over the patient's head, the harness applies forces through the rigid manifold and onto the face contacting part of the mask. The face contacting part is compressed against the patient's face causing a gas tight seal to form between the face contacting part and the patient's face.

Typically, the face contacting part of a conventional respirator mask is made from a soft flexible material such as silicone rubber. While this part will distort in one axis (the Z axis) perpendicular to the plane of the patient's face (that plane being the X-Y or facial plane), this part will typically not distort substantially in the X-Y plane, in use (note that FIG. 1 of the accompanying drawings shows the X, Y and Z axes).

This is due to the typical design features of such masks in which a significant part of the face contacting part is relatively thick, being several millimetres in thickness, making it substantially inflexible under the forces which are normally applied in use through the harness. Further, the face contacting part is generally held in place in a single X-Y plane by the rigid manifold which prevents any distortion of that part in the X-Y plane. Also, the configuration of the harness and mask results in any forces transmitted to the mask being transmitted in the Z direction onto the face contacting part thereby tending not to distort the mask in the X-Y plane.

In one common design of conventional mask, as well as the relatively thicker face contacting part, the mask includes a much thinner face sealing membrane portion attached to the face contacting part. In use, as the face contacting portion is lowered onto a patient's face some areas of the flexible membrane portion will contact some parts of the patient's face before others.

These areas are compressed towards the relatively thicker, less flexible, section of the face contacting part. Once in place, at some sections of the interface between the mask and the patient's face, the flexible membrane is compressed tightly against the relatively thicker portion of the face contacting part, whereas at other sections the membrane seals against the face but floats freely of the relatively thicker portion. The flexible membrane provides a gas tight seal between the relatively thicker portion and the patient's face. In this way, such conventional masks attempt to form a gas tight seal in a diverse range of patients having different facial contours, which vary significantly in their X-Y-Z topography, at the position of the mask interface. Generally speaking, the topography of the face sealing portions of such masks is fixed in the X-Y plane, with the flexible membrane accommodating different facial contours in the Z direction.

Such conventional masks have a number of significant shortcomings. In some cases, patients find them uncomfortable. In particular, the relatively thicker sections of the face contacting part can cause discomfort when pressed against a patient's face at the pressures required to create a gas tight seal. This is a particular problem where high therapeutic gas pressures are required. In other cases, such masks do not fit properly, for example where the mask is too narrow in the X-Y plane for the patient's nose. Often, the bulky rigid manifold and relatively high attachment points of the harness cause a patient's line of vision to be impaired and this can cause a degree of claustrophobia in some patients.

An additional problem arises from the use of rigid materials in mask construction, particularly for the manifold. When a patient wearing a mask having a rigid manifold turns in bed and contacts an object such as a pillow, reaction forces from the pillow tend to push the manifold laterally and lift the face contacting part from the patient's face thereby breaking the gas tight seal and causing an air leak which prevents optimum therapy being delivered to the patient. Hard plastic components may also cause pain or discomfort if they are pushed hard against a patient's skin during sleep.

The use of hard components also makes it difficult for a patient to sleep on their stomach, because pressure on the manifold tends to result in air leakage or patient discomfort. The use of rigid manifolds also requires that a patient removes their mask, if they wish to scratch their nose. The design of many existing masks involves the use of multiple plastic and silicone parts. Such masks can be difficult for some patients to dismantle and clean. In addition parts can become broken or lost. A mask made from many parts is typically more expensive to produce than a mask having fewer parts, due to increased moulding costs for the many different parts, and assembly and inventory costs.

A further problem with existing conventional masks is that a substantial number of patients leak gas from their mouth during positive gas pressure therapy. In particular patients using nasal masks may release gas from their mouths. Typically, pressurised gas will enter a patient's oral cavity and cause the patient's cheeks to stretch and balloon out until their mouth starts to open and the gas pressure is released. Such patients are often treated with full-face masks which deliver positive gas pressure both nasally and orally. In general, these masks are similar in design to conventional masks which only deliver gas nasally. They consist of a rigid manifold part attached to a face contacting part, typically made from a flexible material such as silicone. Full-face masks have a face contacting part designed to encompass both a patient's nose and mouth, providing a gas tight seal at the mask/face interface in order to enable successful delivery of pressurised gas. However one of the problems with these masks for some patients is that they do not succeed in fully preventing gas leakage from the patient's mouth. Often gas leakage is preceded by stretching and ballooning of the patient's cheeks, which tends to substantially change the facial contours adjacent the face sealing portion of the masks. This significant facial deformation has the effect of breaking the gas tight seal around the mask, since the face contacting portion of the mask presents a relatively rigid sealing surface incapable of adapting to such large changes in facial contours.

The present invention seeks to address and attempt to alleviate at least some of the deficiencies of the existing masks described above.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY OF THE INVENTION

In abroad aspect, the present invention provides a mask which has a flexible manifold and face-contacting components which can be distorted into different shapes to suit differing facial contours when applying tensile forces to the mask, typically by means of a straps and a harness. The nature of the connection between the straps and the mask is such that loadings applied to the mask via the straps are distributed so that distortions of the mask under load will not compromise the required air seal between the users face and the face contacting part of the mask.

More specifically the present invention provides a mask for supplying gas under pressure to an airway of a human including:

a flexible manifold shell, being made of a flexible material, the manifold including means for connection to a gas delivery pipe at least two side walls which are at least partially comprised of portions of the manifold shell;

a first mask shape forming element for distributing distortional forces to a substantial portion of one side wall that attaches to or is integral with a significant portion of that one side wall of the mask; and a second mask shape forming element for distributing distortional forces to a substantial portion of another side wall that attaches to or is integral with a significant portion of that other side wall of the mask, each mask shape forming element being connected to, or being connectable to, a strap;

a flexible face contacting element defining a recess to accommodate the nose of the human;

wherein, forces exerted by the first and second mask shape forming elements are, capable of deforming the flexible face forming element and manifold in the X-Y plane to create a variety of different mask/orifice shapes and attitudes.

The mask further comprises: at least a third strap or mask anchoring means disposed between the first and second mask shape forming elements.

The X, Y and Z axes are as defined above in the background of the invention. A significant portion of the side wall is typically at least 50% and most preferably at least 80%, of the extent of the side wall.

The centre of the mask shape forming elements are preferably generally centrally located on each side wall.

The manifold shell should be of sufficient thickness to resist major distortion by elevated pressure present in the mask in use, while being sufficiently flexible to allow the whole mask shape to distort into the variety of different mask/orifice shapes and attitudes particularly when under external load and without compromise to the required seal between the face contacting part and a users face.

It is preferred that the first and second mask shape forming elements are integral with side straps and comprise webs at the ends of the side straps which join the side walls of the mask. The ends of the straps distal from the manifold preferably define a slot or other means for connection of the strap to a harness.

In use, tension on these side straps when pulled laterally in the horizontal plane (X-axis) is transmitted through the mask shape forming elements to the manifold shell and face contacting portion and can cause the general shape of the mask to be in one extreme elongated in the general direction of the lateral tension or alternatively tension applied on these side straps downward in the horizontal direction (Y-axis) with an opposing force applied to the third strap or mask anchoring means causes the shape of the mask to be elongated in the general direction of this horizontal tension.

The third strap is most typically a nasal arch strap which optionally defines at least part of an air inlet pipe.

Preferably, the tensile load transmitted axially through the side straps and via gussets/webs which distribute the axial load along the manifold body.

Preferably the web is tapered inwards in the Y direction and as it locates towards the top region of the manifold.

In an alternative related aspect, the invention may be considered to be a mask incorporating three elements.

A first element of the mask is a flexible manifold shell. This element is disposed on a non-face contacting portion of the mask, encloses the mask and has a connection for a gas delivery pipe that may also be flexible. It is made of a flexible material and is of sufficient thickness to resist major distortion by elevated pressure within the mask. The gas delivery pipe may be connected at the top of the manifold or alternatively it may engage that part of the manifold at the front of the mask.

However it is sufficiently flexible to allow the whole mask shape including the flexible manifold shell and the face contacting element to be distorted into a wide range of general shapes.

A second element of the mask is a mask shape forming element that is used to distribute distortional forces to a substantial portion of the perimeter of the side wall of the mask, the side wall being made up of at least a portion of the manifold shell.

This shape forming perimeter element is connected to a series of straps extending away from the side wall of the mask, generally with at least one strap on each side of the mask and one strap running along the nasal arch of the forehead.

The shape forming element attaches to or is integral to the side wall of the 25 mask. The straps have a mechanism to connect to a harness at one end.

Tension on these side straps, when pulled in the direction of the X-axis is transmitted through the mask shape forming element to the first and third elements and can cause the general shape of the mask to be in one extreme elongated in the general direction of this tension or alternatively tension applied on these side straps downward in the Y direction Y with an opposing force applied to the nasal arch strap causes the shape of the mask to be elongated in the general direction of this horizontal tension.

A third element of the mask is a flexible face contacting element with an orifice to accommodate the nose or mouth and nose of the subject. The orifice approximates the shape of the perimeter of the base of the nose or mouth and nose. The orifice is formed where this third element's surface, furthest from the manifold shell element, curves inwardly towards the centre of the mask in the general X-Y plane to form the gas sealing surface but leaves the nares in unobstructed communication with the inside of the mask.

The face contacting element joins the flexible manifold shell element and/or the shape forming element such that when the side straps are pulled back across the checks in a direction that passes below the ears and the nasal arch flexible strap is pulled toward the top of the head (Z-axis), the mask is pulled onto the face such that the face contacting element orifice encapsulates the subjects nose or nose and mouth and causes the face contacting element to provide an airtight seal between the mask and patient's skin.

This element is flexible enough to allow it to be pulled into a wide range of general mask shapes no as to vary its shape in the X-Y plane. Flexibility is also required in manufacture to enable the mask to be stripped from its mould cavity.

Variation in the direction and magnitude of the forces exerted from the straps through the shape forming element can be used to vary the magnitude of the gas sealing forces exerted between the subjects skin and the flexible face contacting element at different points round this element.

Most preferably, the third strap is a nasal arch strap and a portion of a mask shape forming element is integral to a portion of the gas delivery pipe. Preferably, the manifold is sufficiently flexible to collapse towards the patient's nose when a moderate external force is applied to it.

Preferably the manifold shell, mask shape forming elements, side walls and face contacting elements are integrally moulded in one piece from an elastomeric material such as silicone rubber, with, optionally, at least a part of the side straps and/or the nasal arch strap and/or air inlet pipe.

The mask is also preferably sufficiently flexible to enable a patient to remove it or fix it in position without having to adjust any harness connection points where a harness connects to the straps of the mask.

The face contacting portion of the mask typically defines an inwardly curving 30 gas sealing surface which in use contacts the patient's face. Typically the mask further includes a series of gas bleed holes defined in the manifold shell.

Advantageously, a mask embodying the present invention may be compressed into an approximate ball shape using a moderate level of hand/digital pressure, and may weigh less than 50 grams including the weight of the straps.

It is preferred that the relative thicknesses of different sections of the flexible manifold and/or flexible face contacting portion are varied so as to vary the amount of stretch in different areas of the mask when forces are applied to the mask from the straps through the mask shape forming element in various directions.

Typically the manifold includes ribbing. It is preferred that the interior surfaces of the mask are generally smooth, which makes cleaning of the mask relatively easy. It is preferred that the manifold is flexible enough to collapse toward the patients nose when a moderate external force is applied to it, to allow, for example, a patient to scratch their nose without removing the mask. With the mask in situ, the manifold can be distorted onto the patient's nose without breaking the airtight seal between the face contacting element and the patient's skin. This also means that when a patient turns in sleep and their mask contacts a pillow or some other object the manifold will deform and/or displace rather than be pushed against the patient's face. The mask face contacting element is preferably flexible and allows a rolling reaction in the mask as loadings are applied via the straps. The mask shape forming element may include a planar band which attaches to or is integral to a significant portion of the side wall of the mask. The planar band may be used for assisting in the correct location of the mask by locating on the patient's top lip, in use.

In a preferred embodiment, the mask shape forming element may provide multiple attachment points to the straps and/or flexible mask which can be adjusted in length so as to change the distribution of forces to various areas of the flexible mask, through tension exerted in any specific direction on to the straps.

In a yet further embodiment, the mask shape forming element may have attachment points to the straps and/or flexible mask which can be adjusted in their attachment position so as to change the distribution of forces to various areas of the flexible mask, through tension exerted in any specific direction on to the straps.

In a yet further embodiment, the mask shape forming element may be varied in its relative stiffness at different points around its attachment position to the flexible perimeter of the mask side wall so as to change the distribution of forces to various areas of the flexible mask, due to tension exerted in any specific direction on to the straps.

The adjustable mask shape forming elements may be varied in order to change the flexible mask shape and/or the gas sealing pressure between different parts of the face contacting element and the patient's skin.

The mask is preferably sufficiently flexible to enable a patient to remove it or fix it in position without having to adjust the harness connection points where they connect to the straps.

The mask will typically be used in combination with a device for supplying gas, typically air, at a positive pressure to the patient's mouth, either through the patient's nose or through their nose and mouth.

It is preferred that a means is provided for preventing leakage from the patient's mouth while positive pressure is delivered to the patient's nose.

In use, the shape of the mask during its ongoing operation on the patients face in the general X-Y dimension can be varied by first applying tension to the straps in the general X-Y planar direction, prior to fixing the face contacting element onto the patient's face, in order to form the required mask shape. Then while maintaining the desired shape, an additional downward tension may be applied on the straps in the vertical Z-direction in order to fix the face contacting element on to the patients face. Then the harness tension may be adjusted in order to maintain this desired mask shape in its X-Y-Z dimensions.

It is preferred that, the mask's shape on the patient's face may be changed in situ by applying external pressure to its flexible manifold and/or face contacting portion in order to stop gas leakage from the mask, in use.

In one embodiment, the flexible face contacting portion includes side walls, extending in the general Z-axis direction, one end of the side walls being attached to the first and second elements, the other end being attached to the inwardly curving gas sealing surface of the face contacting element.

In one embodiment, the flexible face contacting portion includes side walls, extending in the general Z-axis direction, one end of the side walls being attached to an inwardly directed generally concertina shaped wall. Either the side walls in the general Z-axis direction or the concertina walls may be connected to the manifold and shape forming elements. The other end of the flexible face contacting element furthest from the mask shape forming elements is attached to the inwardly curving gas sealing surface of the face contacting element.

In an alternative embodiment to that described above, the concertina shaped wall is outwardly directed.

The flexible face contacting element is preferably sufficiently flexible that it substantially collapses onto the patient's face under the normal forces exerted on it by the harness and straps when in situ, in use. The mask will preferably inflate under normal operating pressures when in situ on a patient's face, but will preferably not significantly distend in comparison with the mask's "resting" shape.

It is preferred that the manifold shell has an average wall thickness of less than 2.5 mm, preferably 1 mm to 2 mm, most preferably about 1.5 mm. In a preferred embodiment, the flexible face contacting portion has as average wall thickness of less than 1.5 mm, preferably 0.3 mm to 0.7 mm, most preferably about 0.5 mm.

The side straps may be generally curved to follow the general shape of the contours of a patient's cheeks, in situ.

The face contacting portion may collapse substantially onto the patient's face when located in position on the patient's face with the harness and straps correctly adjusted. The mask will typically collapse inwardly towards the patient's face during normal inspiratory effort when the mask is in position and attached to a positive gas pressure device which is not delivering a positive pressure gas flow.

The manifold will typically inflate to maintain its shape when subject internally to positive gas pressure.

The straps may cover a substantial portion of the patient's cheeks and prevent inflation of the patient's cheeks during delivery of positive airway pressure therapy.

The flexible face contacting portion/element may provide a substantially gas tight seal between the mask and the patient's face when the mask is subject to internal gas pressure.

The mask shape forming element may comprise at least three continuous sections, each attached to a strap, where the sections in total connect to at least 40% of the length of the side wall of the mask.

The mask shape forming element may have multiple connections to the side wall of the mask, with more than one connection attached to some straps, where a portion of the perimeter delineated by the connection points and positions extending 2 cm on either side of these points makes up at least 40% of the total perimeter of the side wall of the mask. Whether the shape forming elements are distributed along the walls of the mask continuously or as a series of point loads there will be an overall length measurement the limits of which define an overall contact length. Thus the loading may be transmitted as a distributed load or as a series of distributed point loads.

When subject to internal positive gas pressure, if leaking occurs between the patient's facial skin and the face contacting portion, the leakage may be stopped by manually distorting the flexible part of the mask while is position and thereby changing the force profile around the mask/sealing surface and/or changing the X-Y sealing plane.

STATEMENTS OF INVENTION

In its broadest form the present invention comprises:
a mask for supplying gas under pressure to an airway of a human including:
a flexible manifold shell, being made of a flexible material, the manifold including means for connection to a gas delivery pipe,
at least two side walls which are at least partially formed by portions of the manifold shell;
a flexible face contacting element defining an orifice to accommodate the nose of the human;
a first connecting strap having a first end connected to the mask and a second end connectable to a mask retaining strap;
a second connecting strap having a first end connected to the mask and a second end connectable to the mask retaining strap;
wherein, the first strap and the second strap engage respective side walls of the mask for distributing opposing distortional forces to a substantial portion of the respective side walls when the mask is in use;
wherein the connection of the straps to the mask allow forces exerted by the first and second straps are capable of deforming the manifold at least along X and Y axes to create a variety of different mask/orifice shapes;
wherein, the manifold of the mask has a manifold height and a centroid; and
wherein the first and second straps engage the mask along a connecting length thereby joining the first and second straps to respective side walls of the mask so that an axis through the centroid normal to the Y axis, intersects with at least part of each strap.

In another broad form the present invention comprises:
a mask for supplying gas under pressure to an airway of a human including:
a flexible manifold shell, being made of a flexible material, the manifold including means for connection to a gas delivery pipe,
at least two side walls which are at least partially comprised of portions of the manifold shell;
a first mask shape forming element for distributing distortional forces to a substantial portion of one side wall that attaches to or is integral with a significant portion of that one side wall of the mask; and
a second mask shape forming element for distributing distortional forces to a substantial portion of another side wall that attaches to or is integral with a significant portion of that other side wall of the mask, each mask shape forming element being connected to, or being connectable to, a strap;
at least a third strap or mask anchoring means disposed between the first and second mask shape forming elements;
a flexible face contacting element defining an orifice to accommodate the nose of the human;

wherein forces exerted by the first and second mask shape forming elements are, in conjunction with the third strap or mask anchoring means, capable of deforming the flexible face forming element and manifold in the X and Y planes to create a variety of different mask/orifice shapes;

characterised in that the manifold of the mask is defined by;

a manifold height extending along a Y axis; and the shape forming elements define a connecting length joining the respective first and second shape forming elements to each wall; wherein a ratio of height of the manifold to connecting length falls within the range 0.8-2.0.

Preferably the mask allows distribution of pressure on the margins along a Z axis to retain a seal at the margins of the mask. The straps may be used to adjust the mask in a case for instance where there is a leak at the bridge.

In another broad form the present invention comprises:

a mask for supplying gas under pressure to an airway of a human including:

a flexible manifold shell, being made of a flexible material, the manifold including means for connection to a gas delivery pipe, at least two side walls which are at least partially comprised of portions of the manifold shell;

a first mask shape forming element for distributing distortional forces to a substantial portion of one side wall that attaches to or is integral with a significant portion of that one side wall of the mask; and a second mask shape forming element for distributing distortional forces to a substantial portion of another side wall that attaches to or is integral with a significant portion of that other side wall of the mask, each mask shape forming element being connected to, or being connectable to, a strap;

a flexible face contacting element defining an orifice to accommodate the nose of the human;

wherein forces exerted by the first and second mask shape forming elements are, capable of deforming the flexible face forming element and manifold in the X and Y planes to create a variety of different mask/orifice shapes;

characterised in that the manifold of the mask is defined by;

a manifold height extending along a Y axis; and the shape forming elements define a connecting length joining the respective first and second shape forming elements to each wall; wherein a ratio of height of the manifold to connecting length falls within the range 0.8-2.0.

According to one embodiment the contact length of the web is determined by the sum of separate contact lengths formed by at least one abbreviation in the web. In each configuration of the web, within the scope of the present invention, a resultant force will act through a centroid of the load distribution.

In another broad form the present invention comprises:

a mask for supplying gas under pressure to an airway of a human including:

a flexible manifold shell, being made of a flexible material, the manifold including means for connection to a gas delivery pipe, at least two side walls which are at least partially comprised of portions of the manifold shell;

a first mask shape forming element for distributing distortional forces to a substantial portion of one side wall that attaches to or is integral with a significant portion of that one side wall of the mask; and a second mask shape forming element for distributing distortional forces to a subs portion of another side wall that attaches to or is integral with a significant portion of that other side wall of the mask, each mask shape forming element comprising a generally triangular shaped web one side of which engages the manifold wall and being connected to, or being connectable to, a strap;

a flexible face contacting element defining an orifice to accommodate the nose of the human;

wherein forces exerted by the first and second mask shape forming elements are, capable of deforming the flexible face forming element and manifold in the X and Y planes to create a variety of different mask/orifice shapes;

characterised in that the manifold of the mask is defined by;

a manifold height extending along a Y axis; and the shape forming elements define a connecting length joining the respective first and second shape forming elements to each wall;

wherein a ratio of height of the manifold to connecting length falls within the range 0.8-2.0; wherein a resultant force applied from distribution of load thorough said web over a predetermined length of web or over a span of point loads applied to the web lies approximately in a middle third of the manifold height to allow the mask to accommodate distortion from such applied load.

Height of the manifold may be taken to refer to that distance from a lowermost wall of the masks which normally engages a face of a wearer to an uppermost wall or apex of the mask which engages a nose bridge of a user.

Connecting length is defined as a distance along a mask wall, (i.e. that part of the wall which extends from the upper lip to the bridge of the nose) between extremities of contact of the shape forming elements and the wall location at which they contact the manifold.

A preferred ratio of manifold height to wall length is in the region of 1.2. A preferred ratio of the web connection length to wall length of the manifold is 0.3 but may fall within the range of 0.3-1.0.

The X, Y and Z axes are as defined above in the background of the invention. A significant portion of the side wall is typically at least 50% and most preferably at least 80%, of the extent of the side wall.

In another broad form the invention comprises: a mask made from a flexible material and having at least one side section including a face contacting part;

wherein, one of the side sections of the face contacting part are provided with a thickening in the walls over at least part of the side section.

Preferably, both side sections of the face contacting part are provided with a thickening in the walls over at least part of the side sections. The wall thickenings may be abrupt or gradual according to design requirements.

BRIEF DESCRIPTION OF THE DRAWINGS

A specific embodiment of the present invention will now be described, by way of example only, and with reference to the accompanying drawings, in which:

FIG. 13a is a front view of a yet further embodiment of a mask in a neutral untensioned or undistorted state;

FIG. 13b is a side view of the embodiment of FIG. 13a;

FIG. 14a is a rear view of the mask of FIG. 13a;

FIG. 14b is a top plan view of the mask of FIG. 13a;

FIG. 15a is a rear view of a yet further embodiment of a mask in a neutral untensioned or undistorted state;

FIG. 15b is a top plan view of the embodiment of FIG. 15a;

FIG. 16a is a front view of the mask of FIG. 15a;

FIG. 16b is a side view of the mask of FIG. 15a;

FIG. 17a is a side view of a yet further embodiment of a mask in a neutral untensioned state;

FIG. 17b is a rear view of the embodiment of FIG. 17a;

DETAILED DESCRIPTION OF PREFERRED EMBODIMENTS

Figure 1:
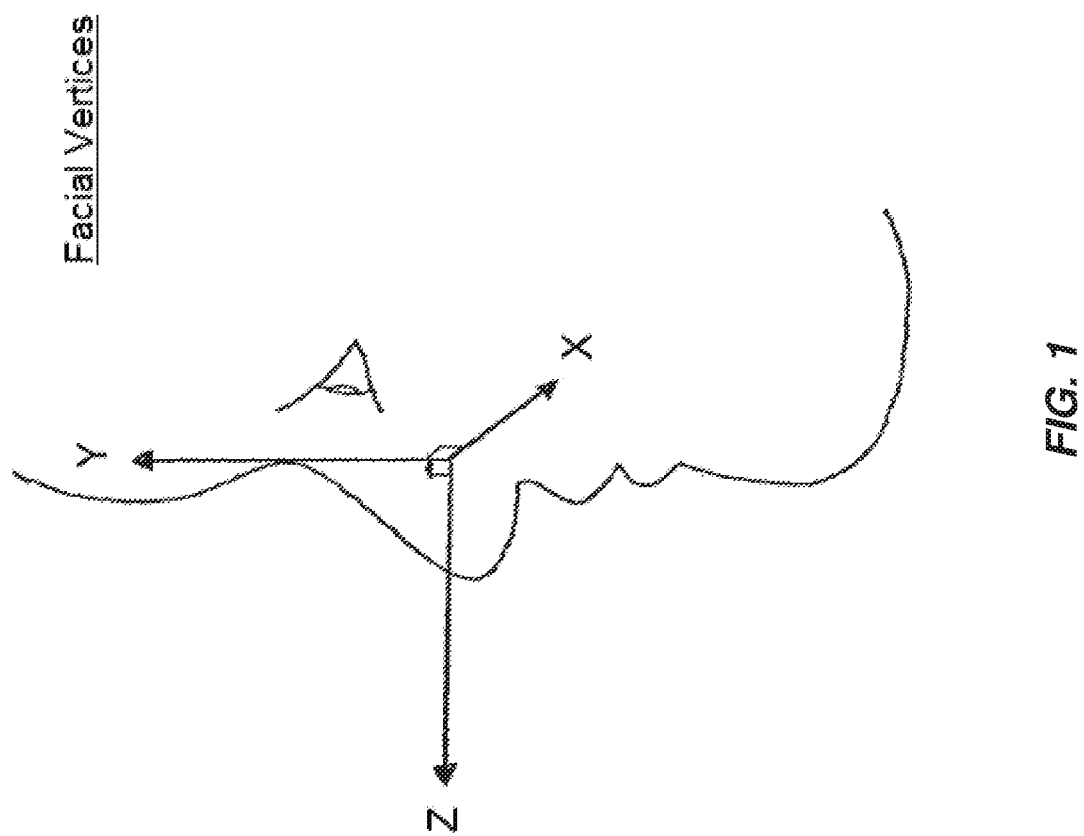
FIG. 1 illustrates the X, Y and Z facial axes of a patient.
Figure 2:
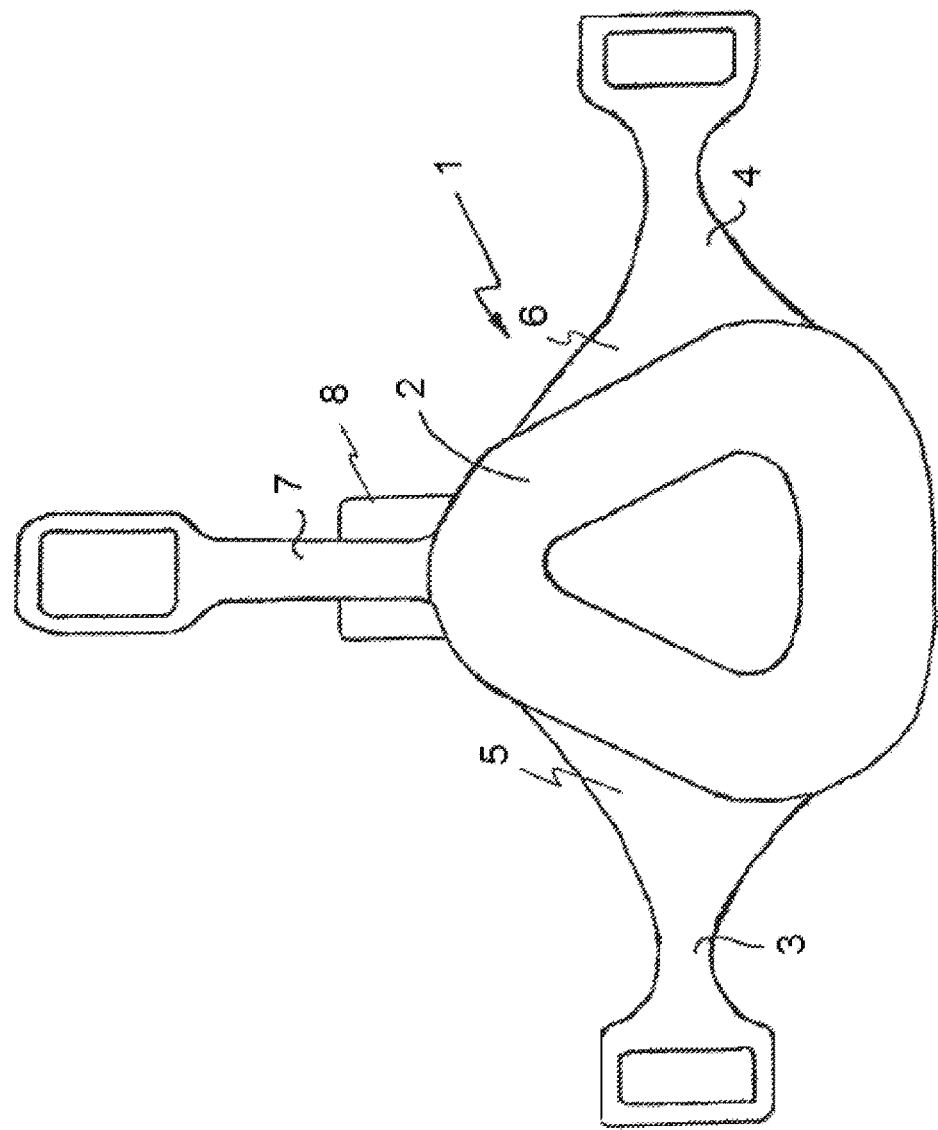
FIG. 2 is a front view of an embodiment of a mask in a neutral un-tensioned state.
Figure 3:
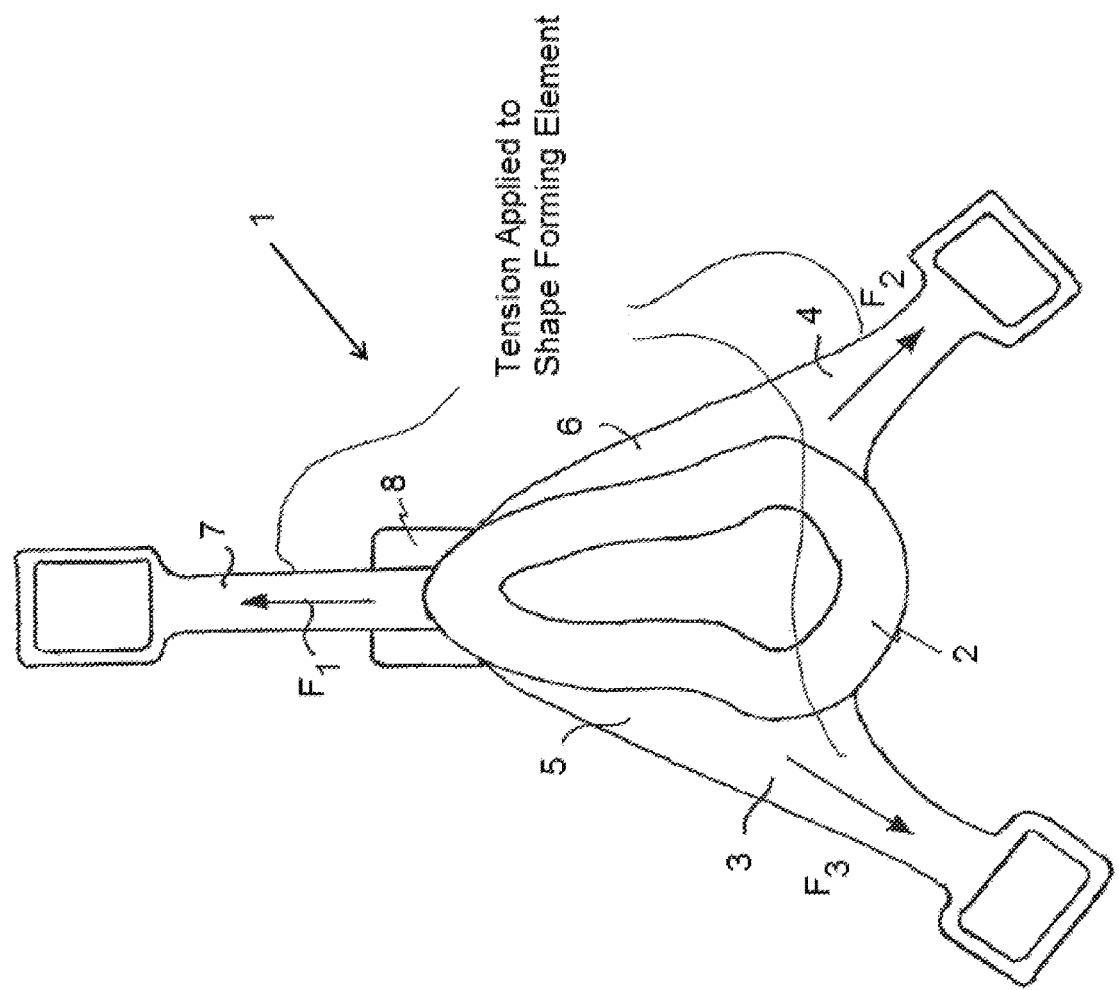
FIG. 3 is a front view of the mask of FIG. 2 showing tension applied to a shape forming element of the mask to stretch the mask in the Y axis.
Figure 4:
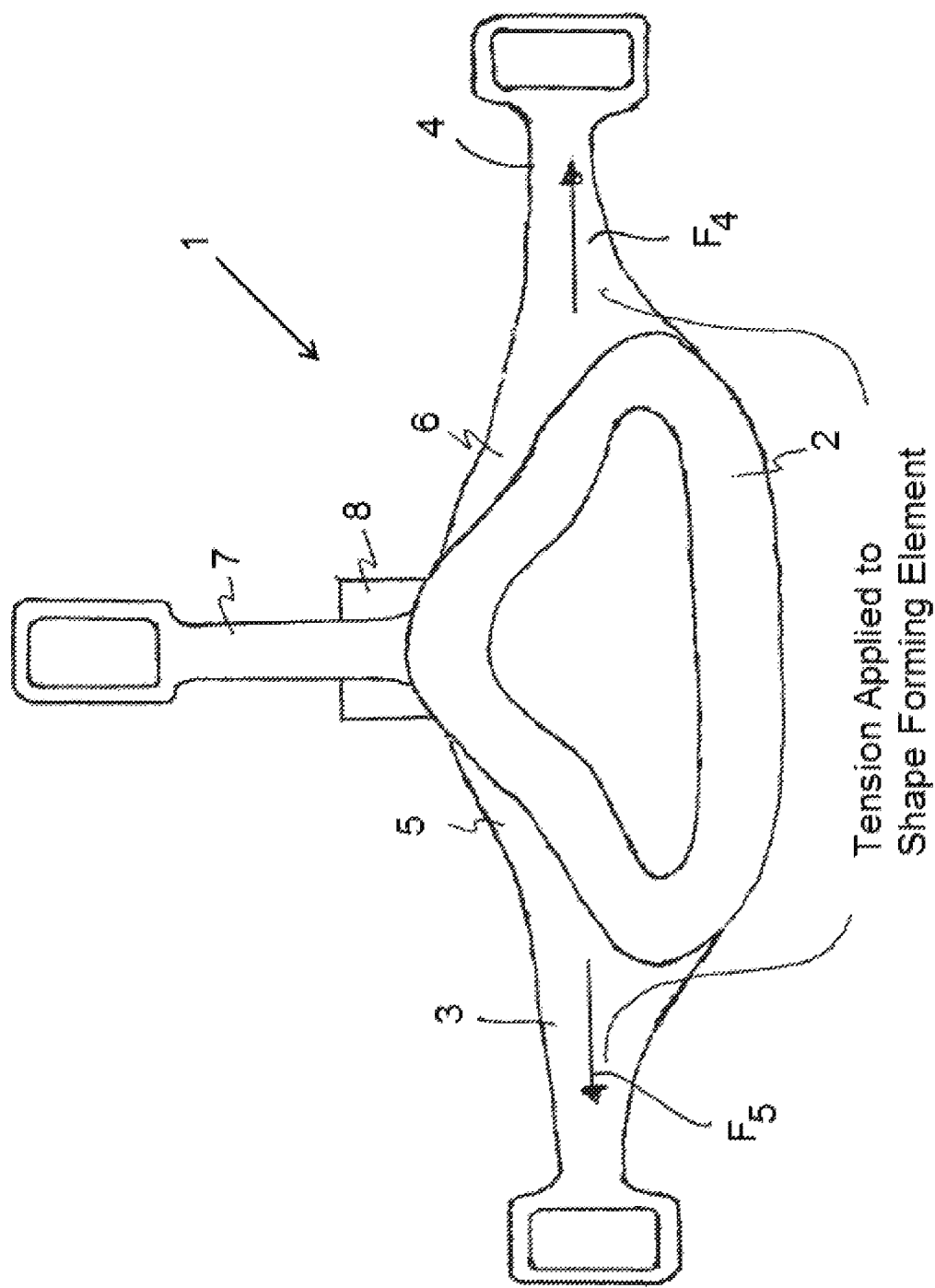
FIG. 4 is a front view of the mask of FIG. 2 showing tension applied to a shape forming element of the mask to stretch the mask in the X axis.

Referring to the drawings, FIG. 1 shows a schematic view of a face indicating the X, Y and Z axes. FIGS. 2 to 10 schematically illustrate a first embodiment of a mask 1 and the principles governing the design and operation of that mask in response to the use of an enlarged web contact portion. FIG. 2 shows a back side elevation of the mask 1. Mask 1 includes a flexible face contacting element 2 and straps 3 and 4. Each of straps 3 and 4 respectively include enlarged web portions 5 and 6 which transfer loads from the straps to the manifold. Mask 1 has been moulded in a single piece from a flexible elastomeric material, most preferably a medical grade silicone. However, any suitable elastomeric material may be used. Mask 1 further includes a third strap 7 and an air inlet 8. The mask of FIG. 1 is shown in a configuration without applied loads. FIG. 3 shows the mask 1 of FIG. 1 with corresponding numbering. The mask in FIG. 3 is shown with straps under a load creating a distortion in the face contacting element 2. FIG. 4 shows the mask 1 of FIG. 2 with opposing loading applied to straps 3 and 4. In this embodiment a resultant force is applied to a manifold (obscured) causing distortion of the face contacting part 2 but without compromising a seal when the mask is attached to a face of a wearer.

Figure 5:
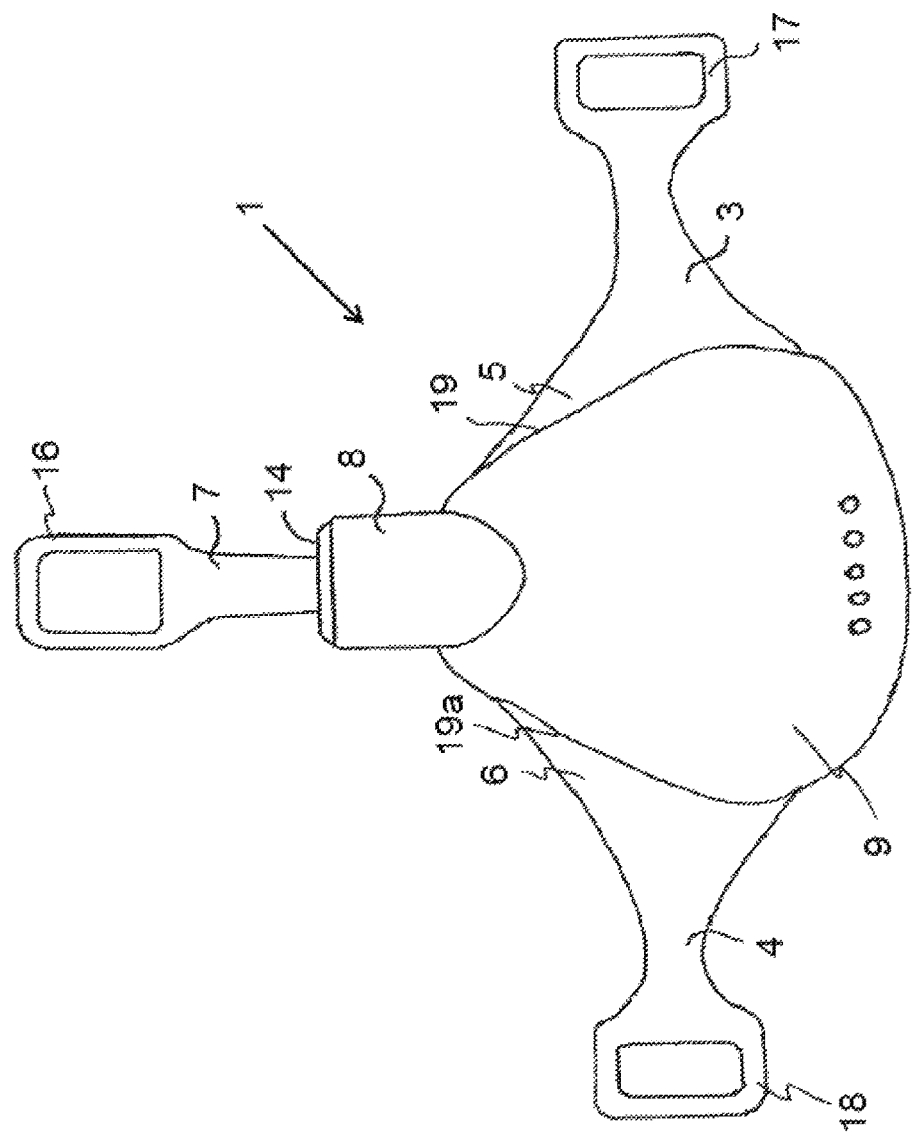
FIG. 5 is a rear view of the mask of FIG. 2 in a neutral un-tensioned state.

FIG. 5 shows the mask 1 of FIG. 2 from the opposite side and with corresponding numbering. The mask in FIG. 5 is shown with straps unloaded and with the manifold 9 in a neutral position. under a load creating a distortion in the face contacting element 2. Mask 1 includes a flexible central manifold 9 and a flexible integral face contacting element 2. An annular air inlet pipe 14 extends away from the manifold 9 to a generally cylindrical outlet 15 at a distal end of the air inlet pipe 14. A nasal bridge strap 16 extends away from the top of the manifold 1. Two straps 3 and 4 extend away from opposite sides of the manifold 9 in a direction which is generally perpendicular to the longitudinal axis of the nasal bridge strap 16. The distal ends of straps 3 and 4 includes connecting tabs 17 and 18 for attaching the mask to a harness. As shown in FIG. 5, the proximal ends of the straps at webs 19 and 19 a where the straps meet the sides of the manifold 9 are relatively wide and in this non limiting embodiment the extent of the strap at its proximal end extends almost the entire length of the side of the manifold 9.

The wall thickness of the manifold and face contacting portion 2 is thin enough to enable patients to stretch and compress different parts of the mask through the application of forces from the harness with a magnitude normally used with current conventional respirator masks. However, the wall thickness while relatively thin is also large enough to withstand therapeutic gas pressures. The distortional forces applied to the mask from the harness are distributed around the body of the flexible mask using a mask shape forming component, which is integral to (or may be attached to) the sidewall of the mask. The shape-forming components (webs) are designed to distribute distortional forces to a substantial portion of the mask sidewall. These forces are then transmitted from the mask sidewall to the remainder of the mask body. This outcome may be achieved using a range of shape forming component designs, although in the embodiment of FIGS. 2 to 10, the mask shape forming elements comprise the proximal ends (webs 19 and 19 a) of the straps 3 and 4 in particular, where they meet the side wall of the mask/manifold.

Figure 6:
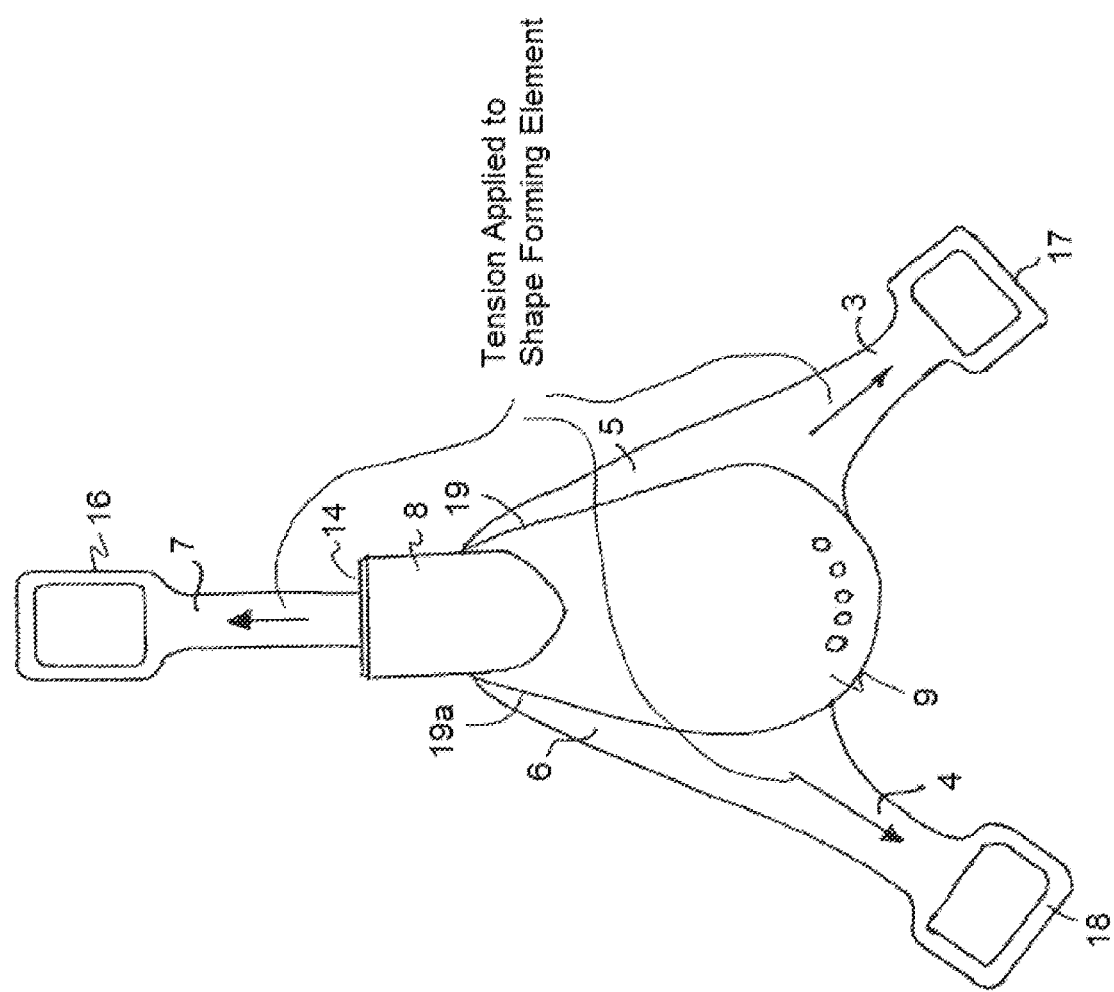
FIG. 6 is a rear view of the mask of FIG. 5 showing tension applied to a shape forming element of the mask to stretch the mask in the Y axis.

FIG. 6 shows from an opposite side the mask 1 of FIG. 3 with opposing loading applied to straps 3 and 4. In this embodiment a resultant force is applied to a manifold 9 causing distortion of the face contacting part 2 but without compromising a seal when the mask is attached to a face of a wearer.

Figure 7:
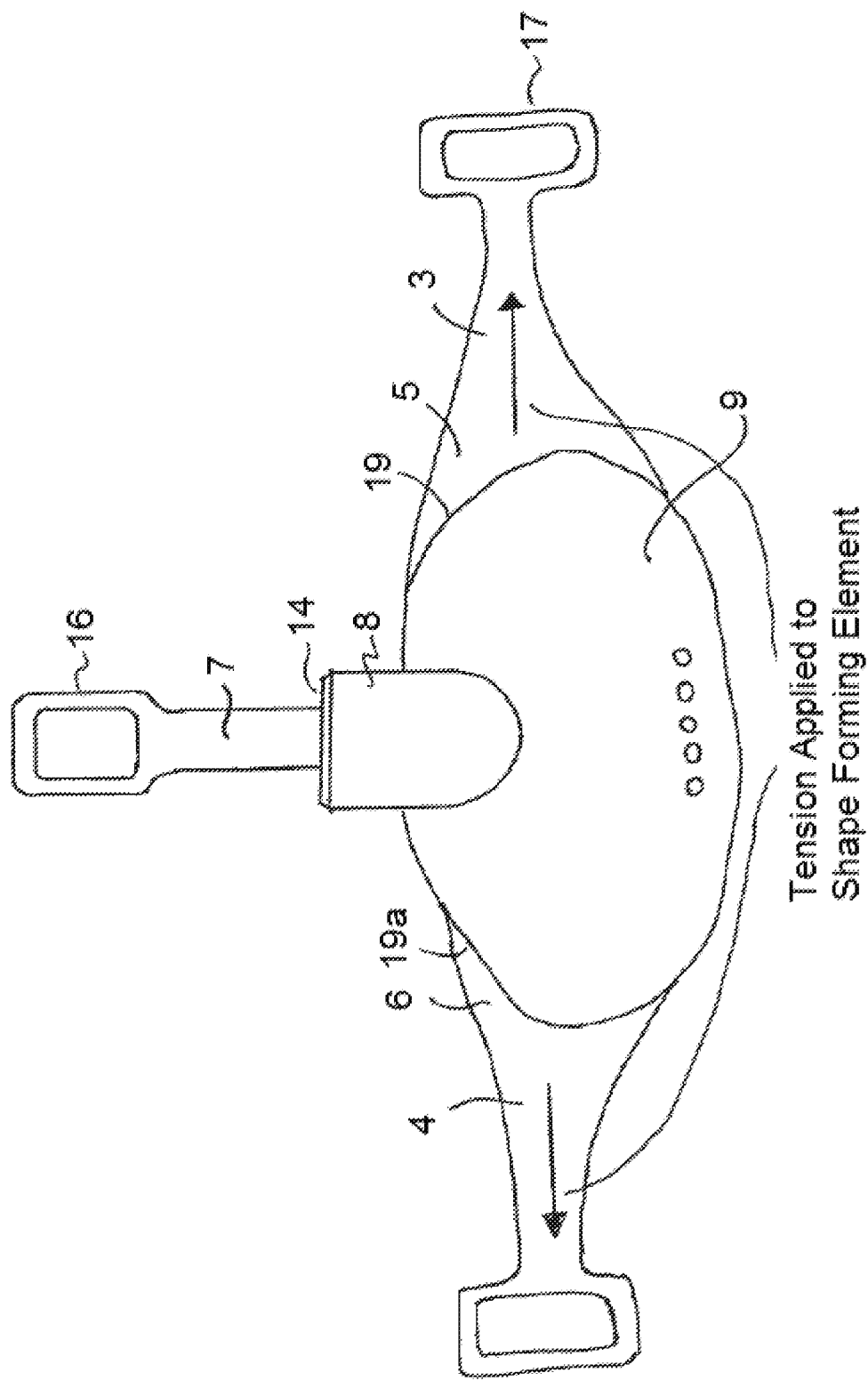
FIG. 7 is a rear view of the mask of FIG. 5 showing tension applied to a shape forming element of the mask to stretch the mask in the X axis.

FIG. 7 shows from an opposite side the mask 1 of FIG. 4 with opposing loading applied to straps 3 and 4. In this embodiment opposing forces are applied to the straps 3 and 4 causing a distortion in the manifold 9.

Figure 8:
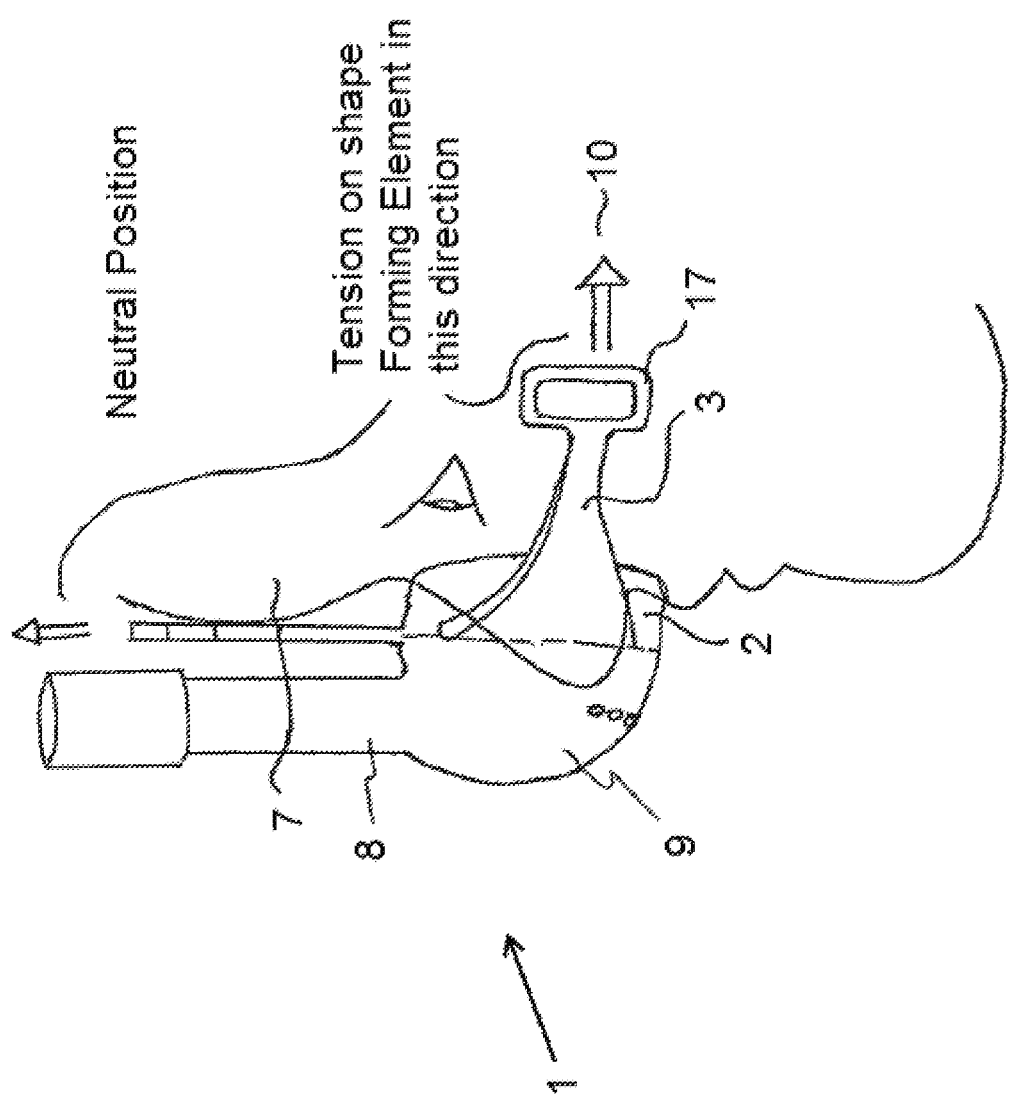
FIG. 8 is a side view of the mask of FIG. 2 in a neutral un-tensioned state.
Figure 9:
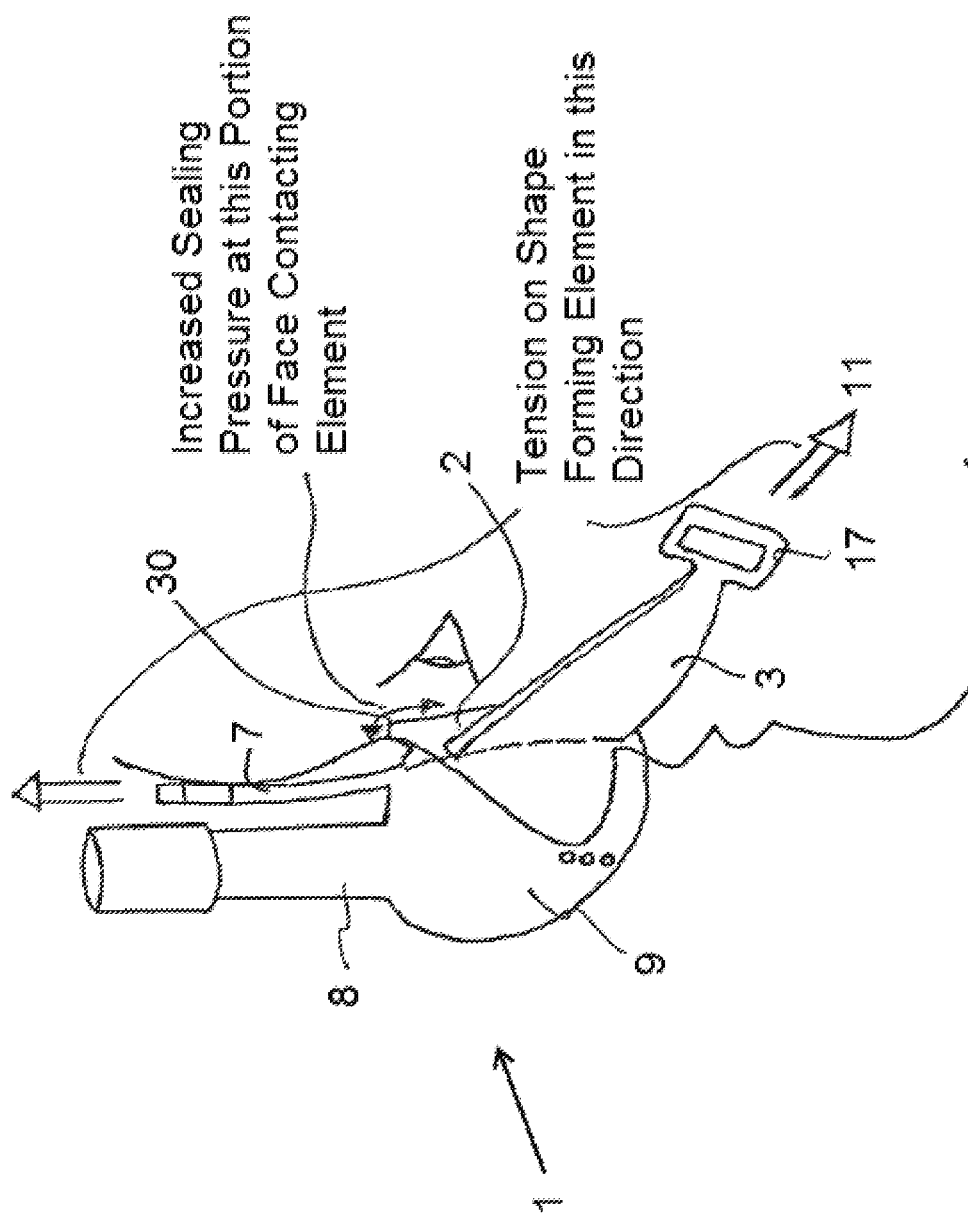
FIG. 9 is a side view of the mask of FIG. 5 showing tension applied to a shape forming element of the mask to stretch the mask in the Y axis.

FIG. 8 is a side view of the mask of FIG. 2 in a neutral un-tensioned state and with corresponding numbering. Loading on the shape forming element (strap 4) is in the direction of arrow 10. FIG. 8 is a schematic side view of the mask in a "neutral" position illustrating that when generally equal tensile forces are applied to the mask, via straps 3, 4 and 7 with the forces applied to the side straps being generally perpendicular to the nasal bridge strap 7. FIG. 9 is a side view of the mask of FIG. 8 showing tension applied in the direction of arrow 11 to a shape forming element (strap 4) of the mask 1 to stretch the mask along the X and Y axes. FIG. 9 illustrates that where the straps 3 and 4 are pulled downwardly at an obtuse angle to the nasal bridge strap 18, increased sealing pressure occurs at the top portion 30 of the face contacting element, adjacent to the bridge of the patient's nose.

Figure 10:
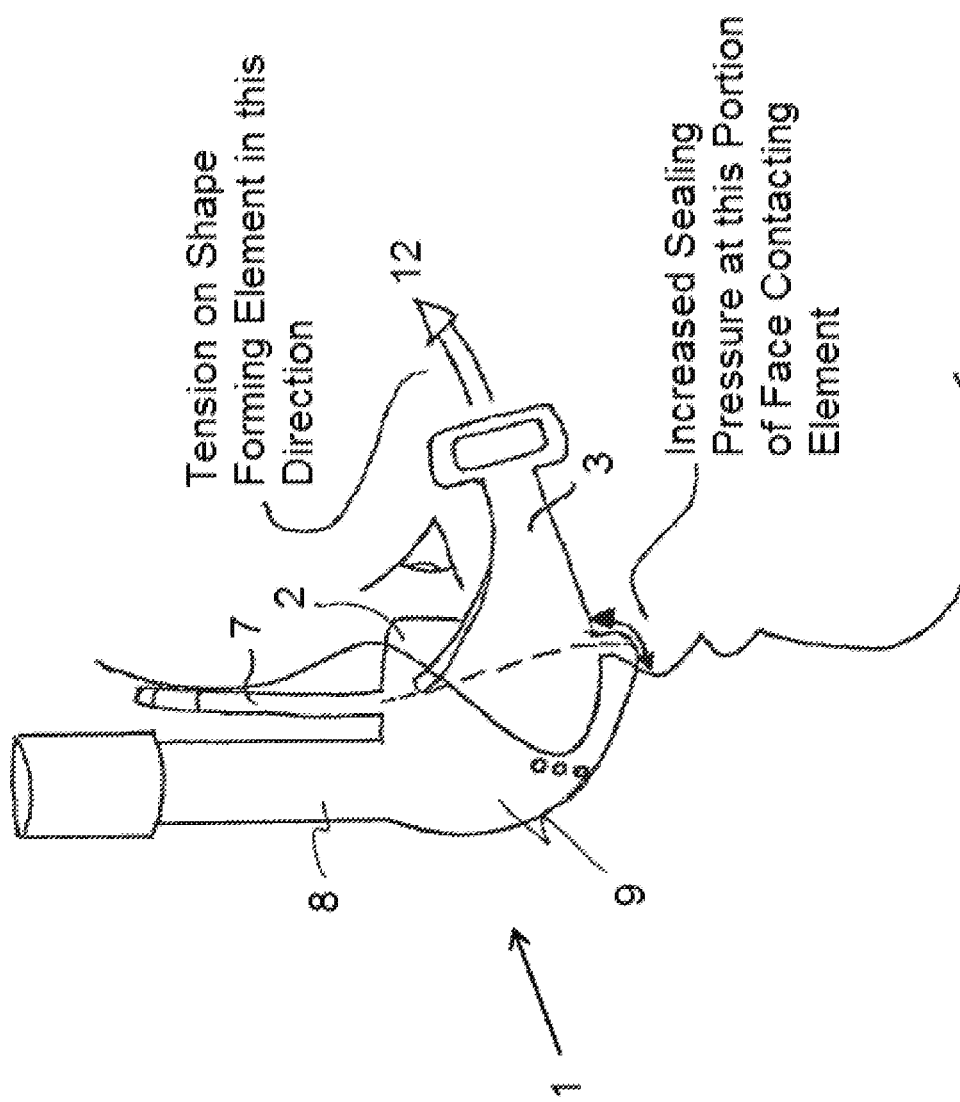
FIG. 10 is a side view of the mask of FIG. 5 showing tension applied to a shape forming element of the mask to stretch the mask in the X axis.

FIG. 10 is a side view of the mask of FIG. 8 showing tension applied to the shape forming element (strap) 4 of the mask 1 in the direction of arrow 12 to stretch the mask along the X axis. This increases sealing pressure at the upper lip region 13 of the face contacting part 2.

Figure 11:
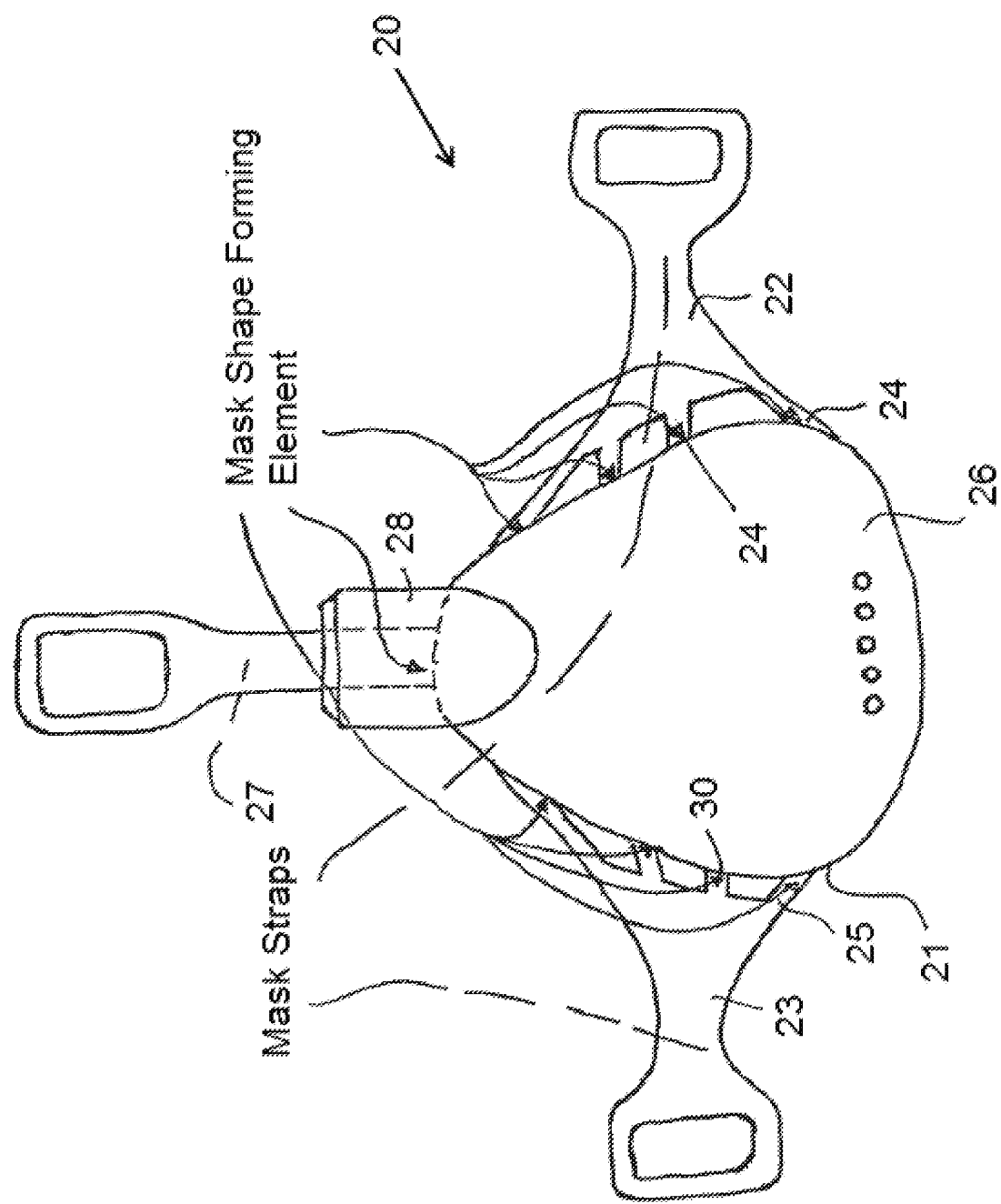
FIG. 11 is a front view of a yet further embodiment of a mask in a neutral un-tensioned or un-distorted state.

FIG. 11 shows a front view of a mask 20 according to an alternative embodiment in a neutral untensioned or undistorted state. Mask 20 includes a flexible face contacting element 21 and straps 22 and 23. Each of straps 22 and 23 respectively include enlarged web portions 24 and 25 which transfer loads from the straps to the manifold 26. Mask 20 is moulded in a single piece from a flexible elastomeric material, most preferably a medical grade silicone. Mask 20 further includes a third strap 27 and an air inlet 28. Mask 20 is shown in a configuration without applied tension loads to straps 22 and 23 inducing distortion. Webs 24 and 25 are characterised in having a series of point load connections at the walls of manifold 26. Web 24 terminates in point connections 29 and web 25 terminates in point connections 30.

Figure 12:
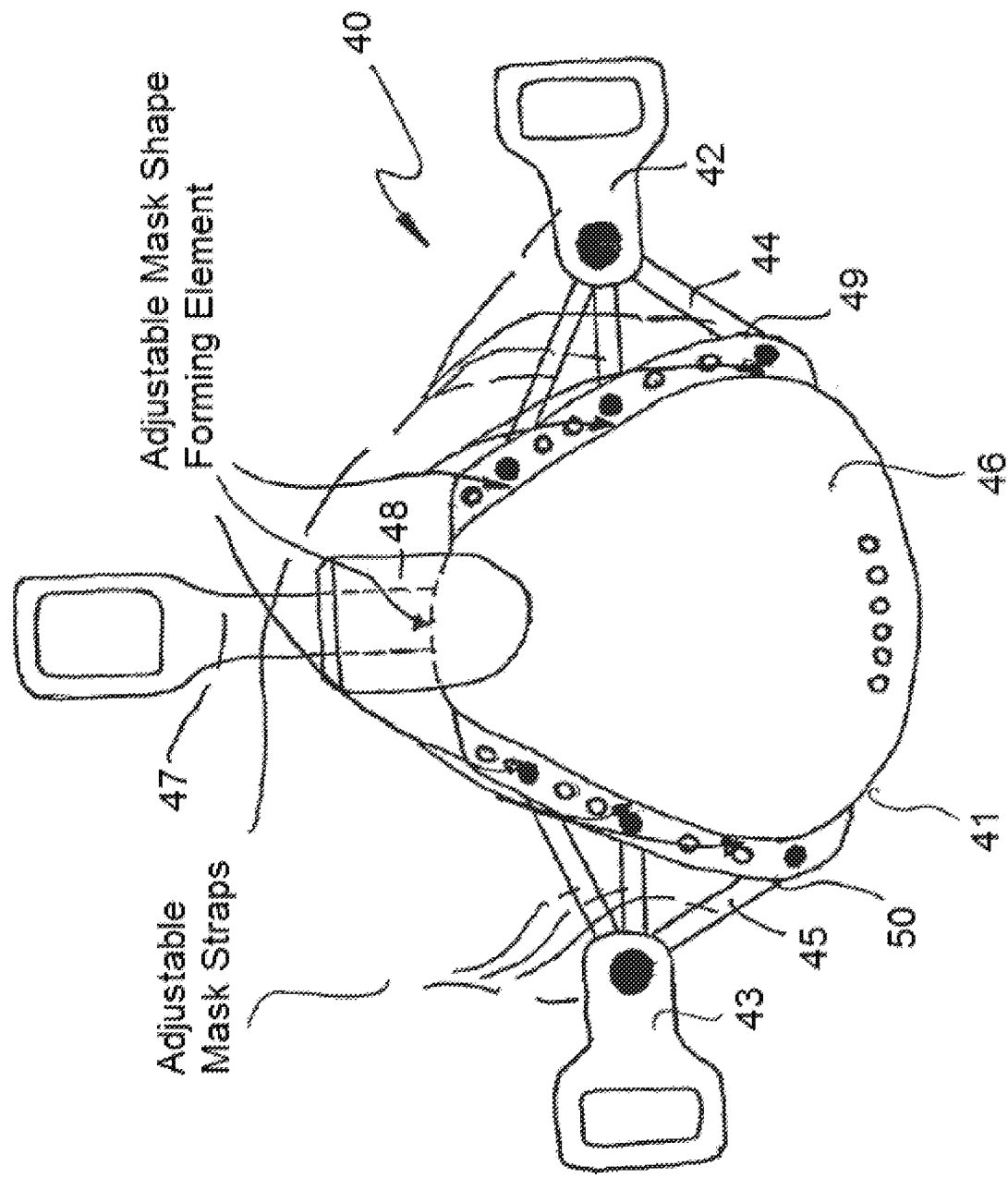
FIG. 12 is a front view of a yet further embodiment of a mask in a neutral un tensioned or undistorted state.

FIG. 12 is a front view of a yet further embodiment of a mask in a neutral untensioned or undistorted state, shows a front view of a mask 40 according to an alternative embodiment in a neutral untensioned or un distorted state. Mask 40 includes a flexible face contacting element 41 and straps 42 and 43. Each of straps 42 and 43 respectively include enlarged web portions 44 and 45 which transfer loads from the straps to the manifold 46. Mask 40 is moulded in a single piece from a flexible elastomeric material, most preferably a medical grade silicone. Mask 40 further includes a third strap 47 and an air inlet 48. Mask 40 is shown in a configuration without applied tension loads to straps 42 and 43 inducing distortion. Webs 44 and 45 are characterised in having a series of point load connections at the walls of manifold 46. Web 44 terminates in point connections 49 and web 45 terminates in point connections 50.

Figures 14A, 14B:
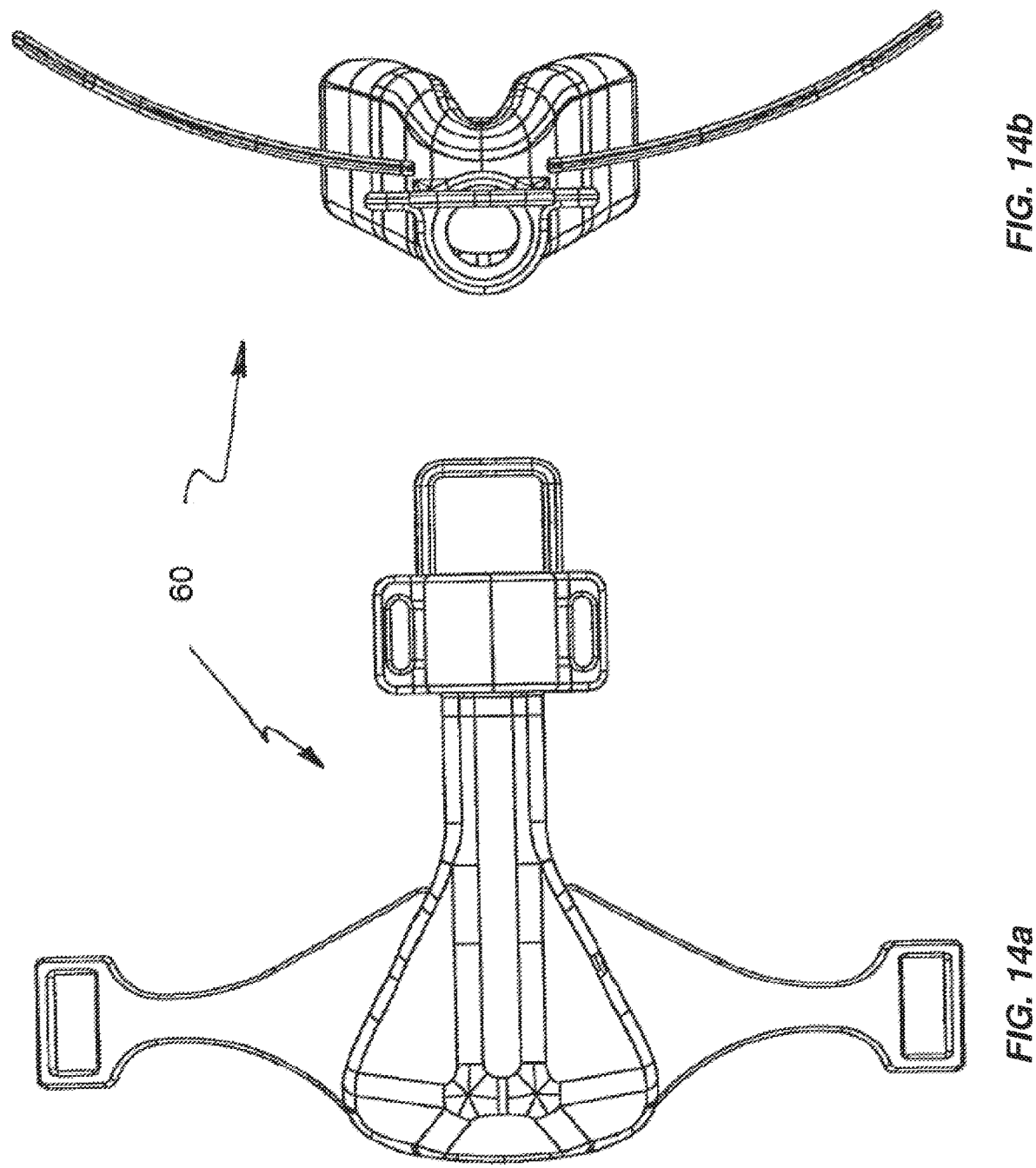

A more detailed description of the construction of other embodiments follows the description of FIG. 14a and later Figures. The mask 10 is designed for pressurised gas delivery to a patient's nose only.

FIGS. 2 to 7 show how the mask may be distorted in the X-Y plane by application of forces to the straps. FIGS. 2 and 5 shows the mask in a "neutral" position where no tension is applied to the shape forming element via the straps 3 and 4. FIGS. 3 and 6 show how the mask distorts when tensile forces F1, F2, F3 are applied to all three straps. In this example the mask becomes elongated in the Y-axis and compressed in the X-axis, suiting a patient with a long thin nose. FIGS. 3 and 6 show tensile forces F4 and F5 applied to the shape forming element via the side straps 3 and 4. In this example the mask becomes elongated in the X axis and compressed in the Y-axis, suiting a patient with a relatively wide nose.

FIGS. 8 to 10 show how the application of forces in different directions through the straps affects the forces exerted by the face contacting portion 2 on the patient. This contrasts with existing masks where the face contacting portion is relatively fixed in the X-Y plane. FIG. 10 illustrates that where the straps 3 and 4 are pulled more upwardly at an acute angle to the nasal bridge strap 7, increased sealing pressure occurs at the bottom portion 2 a of the face contacting element 2, adjacent to the patient's nares.

Hence, in addition to being able to change the shape of the mask, its flexible 30 nature allows patients to adjust the sealing forces between the face contacting portion and the patient's skin at various points around the perimeter of the mask. In particular, it is possible to adjust the relative size of those forces at different points around the face contacting portion. This is also achieved by varying the forces applied to specific areas of the face contacting portion by adjusting the level and direction of forces applied to the mask from the harness.

FIGS. 11 and 12 show variants of the mask in which different shape forming elements are provided. In the mask of FIG. 12 the end of the strap 20 proximal to the side wall of the mask where the strap connects to the side wall is split into four spaced apart fingers 34 which attach to the side wall at four respective points spaced along the length of the side wall. The other strap 22 is attached in the same way. In FIG. 13 the shape forming element of the mask 10b is adjustable. In particular there is an integrally formed flange 36 which extends along the length of each side wall of the mask 10 b. A series of spaced apart holes 38 are defined along the length of each flange 36. In this case the straps 40 for attachment to a harness define a plurality of fingers 42 which are pivoted to the straps 40. The end of each finger distal from the pivot defines a protrusion which push or snap fits into a hole in the flange. The attachment points of the fingers on the flange may be changed to adjust the effect of tension applied to the straps 40 and the distribution of tensile forces to the mask body.

Variation of the relative thickness of wall sections throughout the mask will also is change the amount of stretch or compression achieved at these positions through the administration of any given magnitude and direction of forces through the shape forming element. Variation of mask wall thickness would typically be achieved by variation of the moulds used for mask production. The forces of the mask may be altered by changing the size and/or direction of forces on the straps.

There are a number of preferred embodiments of the mask for covering the nose only, each of which is made from a single component including the mask manifold, face contacting component, mask shape forming component, gas tubing connector and straps (see FIGS. 14 to 18).

FIG. 13a shows a rear elevation of a mask 60 according to an alternative embodiment. FIG. 13b shows the mask of FIG. 13a rotated 90 degrees. Mask 60 includes a flexible face contacting element 61 and straps 62 and 63. Each of straps 62 and 63 respectively include enlarged web portions 64 and 65 which transfer loads from the straps 62 and 63 respectively to the manifold 66. Mask 60 has been moulded in a single piece from a flexible elastomeric material, most preferably a medical grade silicone. However, any suitable elastomeric material may be used. Mask 60 further includes a third strap 67 and an air inlet 68. The mask of FIG. 13a is shown in a configuration without applied loads and further comprises a gas inlet pipe 68 and nasal bridge strap 69 which are integrally constructed. FIG. 14a is a rear view of the mask 60 of FIG. 13a and FIG. 14b is a top plan view of the mask 60 of FIG. 13a with corresponding numbering.

Figures 15A, 15B:
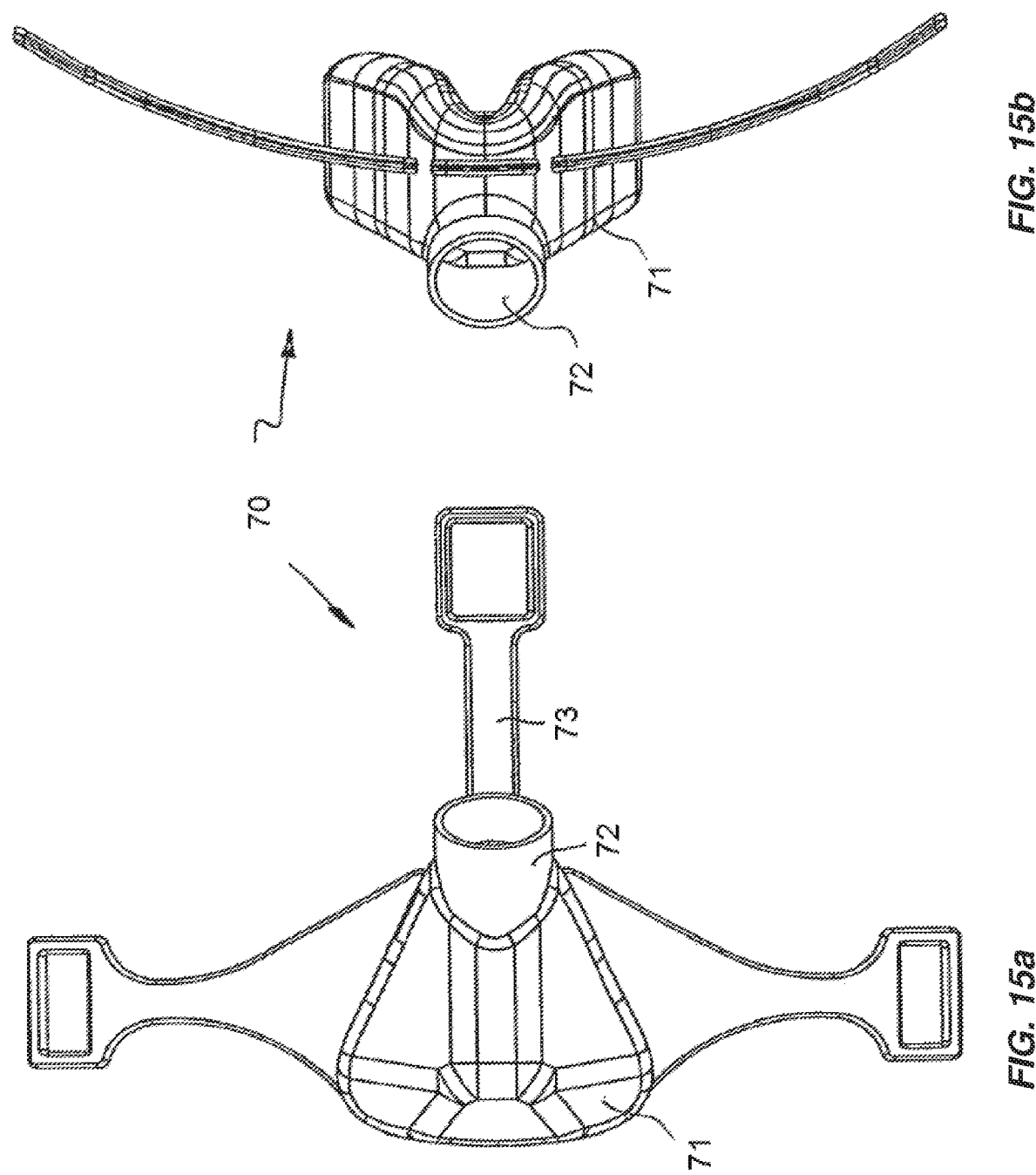
Figure 16B:
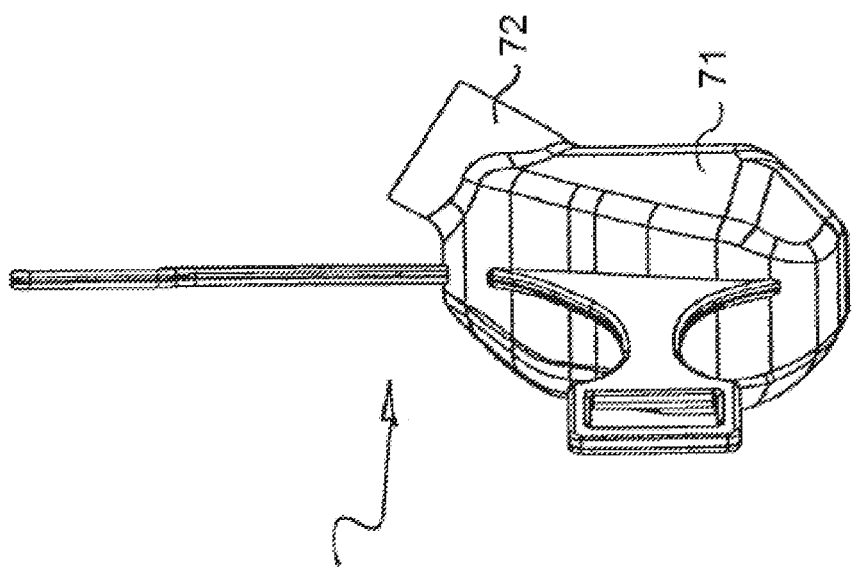
Figure 16A:
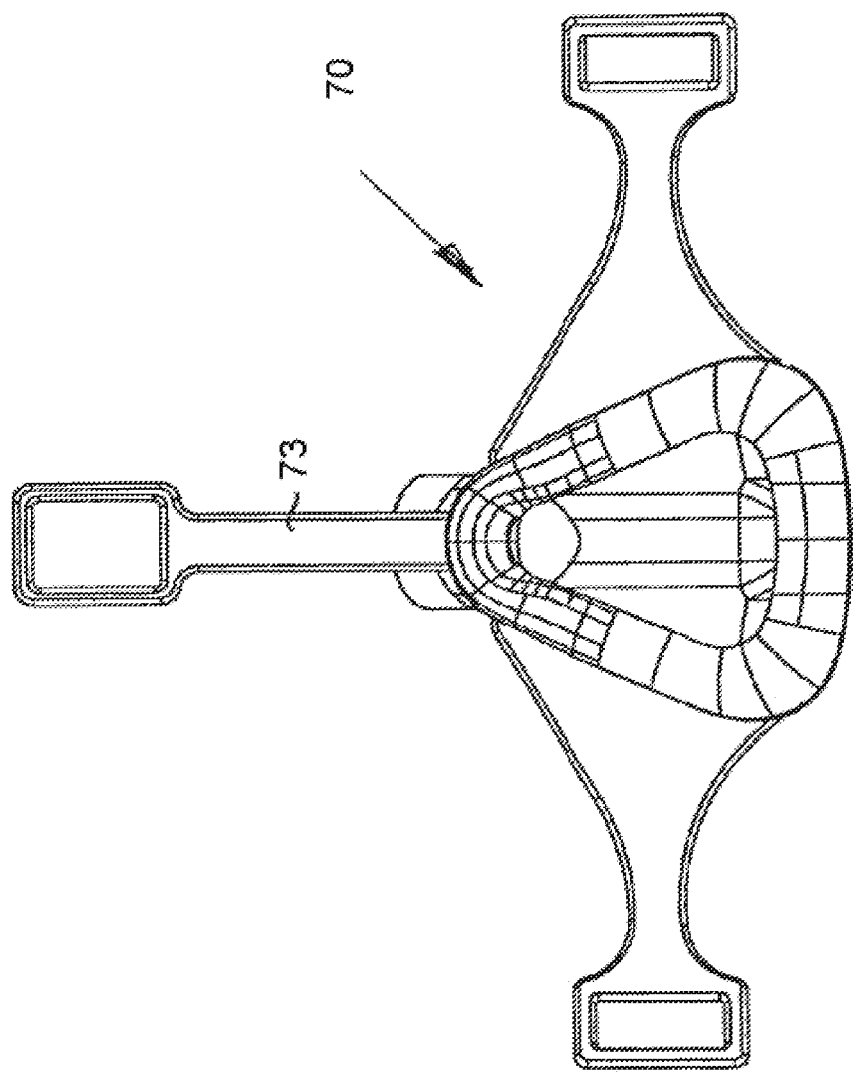
Figure 18:
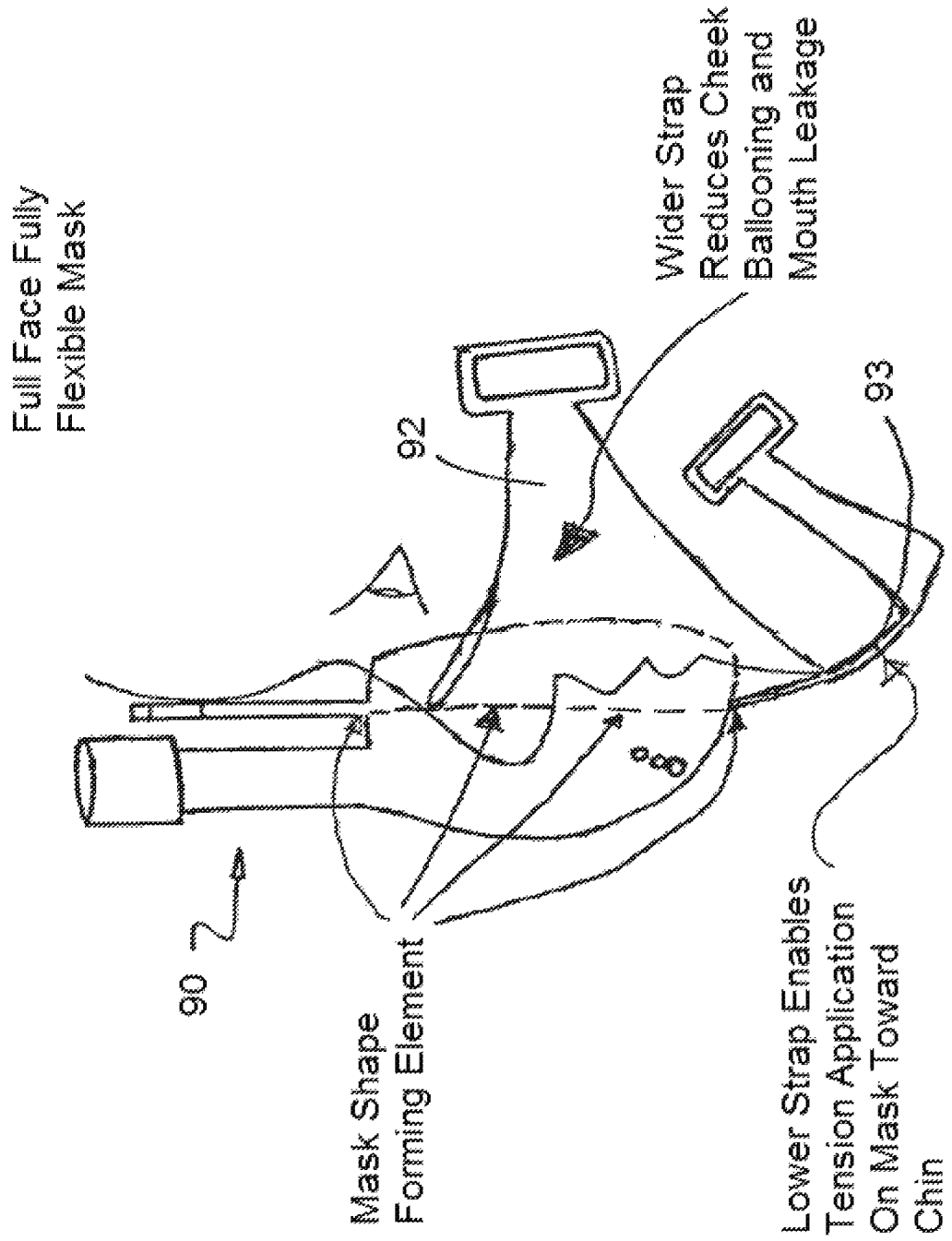
FIG. 18 is a side view of a full-face mask embodying the present invention.

FIG. 15a shows a front elevation of mask 70 and FIG. 15b shows a plan view of the mask of FIG. 15a Mask 70 comprises a manifold 71 including a gas inlet pipe 72 and the nasal bridge strap 73. FIG. 16a is a front view of the mask 70 of FIG. 15a. FIG. 16b is a side view of the mask 70 of FIG. 15a.

FIG. 17a is a side view of a yet further embodiment of a mask 80 in a neutral untensioned state. FIG. 17b is a rear view of the embodiment of the mask 80 of FIG. 17a. In mask 80 shown in FIGS. 17a and 17b, the face-contacting component incorporates a flexible concertina section or groove 81. Mask 80 includes a flexible face contacting element 81 and straps 82 and 33. Each of straps 82 and 83 respectively include enlarged web portions 84 and 85 which transfer loads from the straps 82 and 83 respectively to the manifold

86. Mask 80 has been moulded in a single piece from a flexible elastomeric material, most preferably a medical grade silicone and further includes a third strap 87 and an air inlet 88. The mask of FIGS. 17*a* and 17*b* is shown in a configuration without applied loads and further comprises nasal bridge strap 89 which is integrally constructed.

In all three masks 60, 70 and 80 the face-contacting component is flexible enough that it substantially collapses down onto the patient's face, which facilitates the formation of an airtight seal between this component and the patients face. This feature enables it to conform to a range of contours along the Z-axis of the face, which vary substantially from patient to patient.

These versions provide a number of advantages in comparison to many current conventional masks. They are more comfortable because they are made totally from soft flexible silicone. In addition they weight significantly less so that the patient is less aware of the mask on their face (i.e. less than 50 gm versus more than 100 gm for many current conventional masks.

The profile is generally smaller on the patient's face resulting in less of their field of view being blocked by the mask. This tends to reduce the feeling of claustrophobia that some patients feel.

Each mask size can potentially fit a wider range of patient's faces due to the ability to substantially distort its shape in the X, Y and Z directions. There is less likelihood of breakage because there are no hard plastic components.

The cleaning process is simplified since it is not necessary to dismantle the mask and there are less crevices, which can hold dirt and micro-organisms. If required the whole mask can be sterilized by autoclaving whereas this is not possible with many existing plastic mask components. The mask can be adjusted to change the shape of the mask and sealing forces around the face sealing interface if leakage occurs, without taking the mask off, or adjusting the harness connectors.

The patient can sleep with the mask in contact with objects such as a pillow. In comparison with conventional masks, the resultant forces applied to the mask by the object do not tend to cause the face-sealing surface to lift off the face and result in gas leakage. This is because the applied force tends to distort the manifold shape rather than lift the mask off the face. The patient can remove the mask without having to disconnect the harness because the mask, straps and harness are flexible and soft and can therefore stretch and be removed from the face without discomfort. This is useful if a patient wishes to remove and replace the mask at night in the dark.

If a patient has discomfort on the skin under the mask (such as an itch) they can massage or scratch it by distorting the mask manifold or other components on the affected part and massaging it through the mask wall.

In a mask developed specifically for covering both the nose and mouth the advantage of having a fully flexible version, compared to conventional masks, is even more significant than in the case of the version for covering the nose only. As discussed above, the facial contours around the perimeter of the nose vary significantly from patient to patient. However, the contours of the facial tissue of any specific patient tend not to change during the night since they are fixed by the underlying bone structure. In contrast, the contours around the facial tissue of the perimeter of the mouth and nose together vary significantly from patient to patient and in addition vary for each patient as they move their jaw relative to their nose. A mask which is flexible in 3 dimensional space will distort its shape as the patient's jaw moves relative to their nose. The ability of the masks face contacting part to move in real time in the X, Y and Z directions, as the patients facial contours change, enables this new mask to prevent mask leakage.

Figure 19:
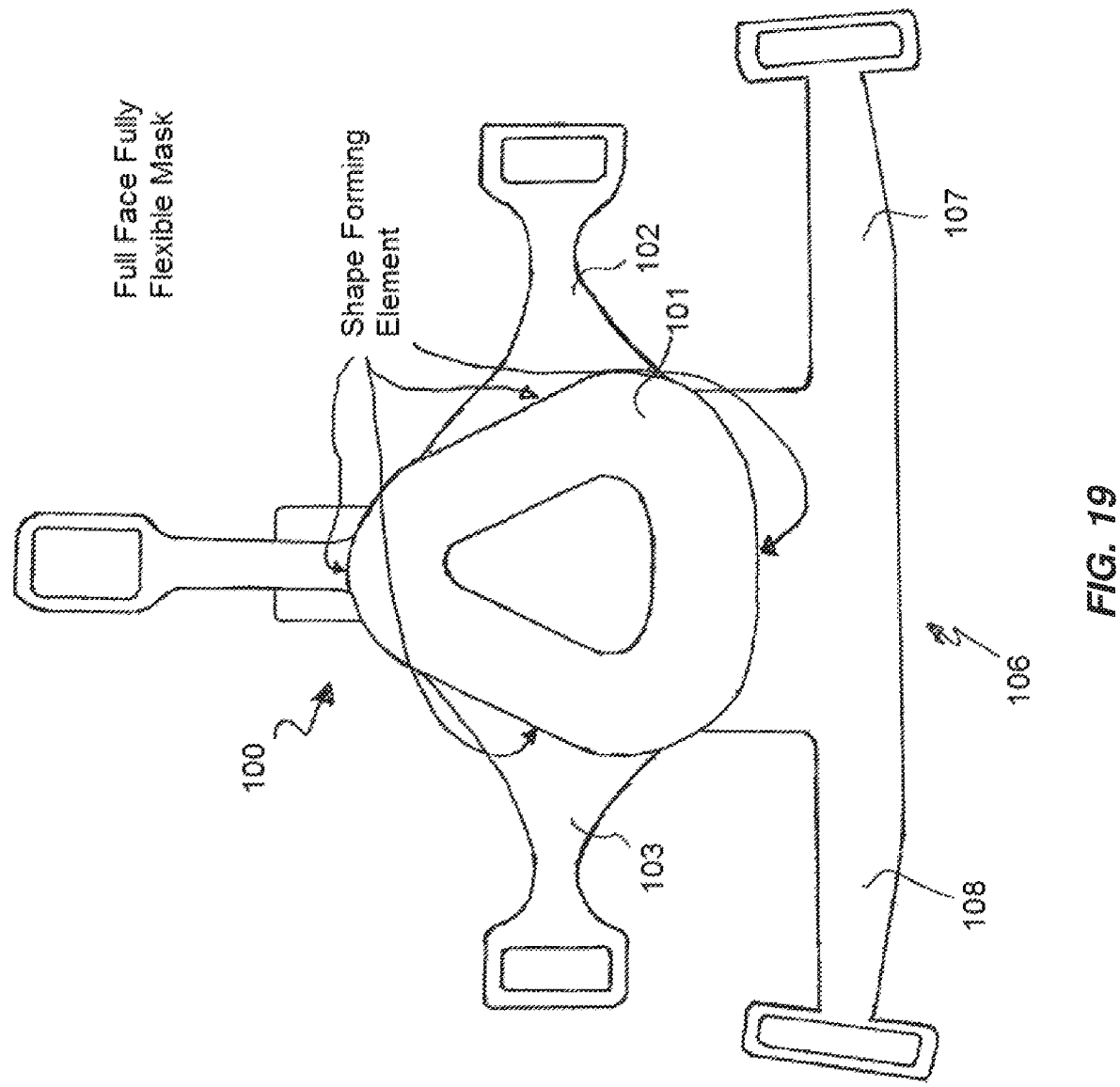
FIG. 19 is a front view of the mask of FIG. 18.

FIG. 19 shows a full face mask 90 in situ on a patient's face 91. The manifold shape forming elements, which are webs 92 according to a preferred embodiment, are largely the same as the mask of FIGS. 2 to 10 but are larger so that they encompass the patient's mouth and nose. However, in this preferred version, in addition to its attachment around the perimeter at the sides and top of the mask, the shape forming element also attaches to a significant portion of the bottom perimeter of the mask. At this point an additional lower strap section 93 pulls this lower portion towards the patients chin. In this embodiment the side straps 92 also cover a significant portion of the patient's cheeks thereby reducing the ability of the cheeks to balloon and leak due to internally delivered gas pressure.

Figure 20:
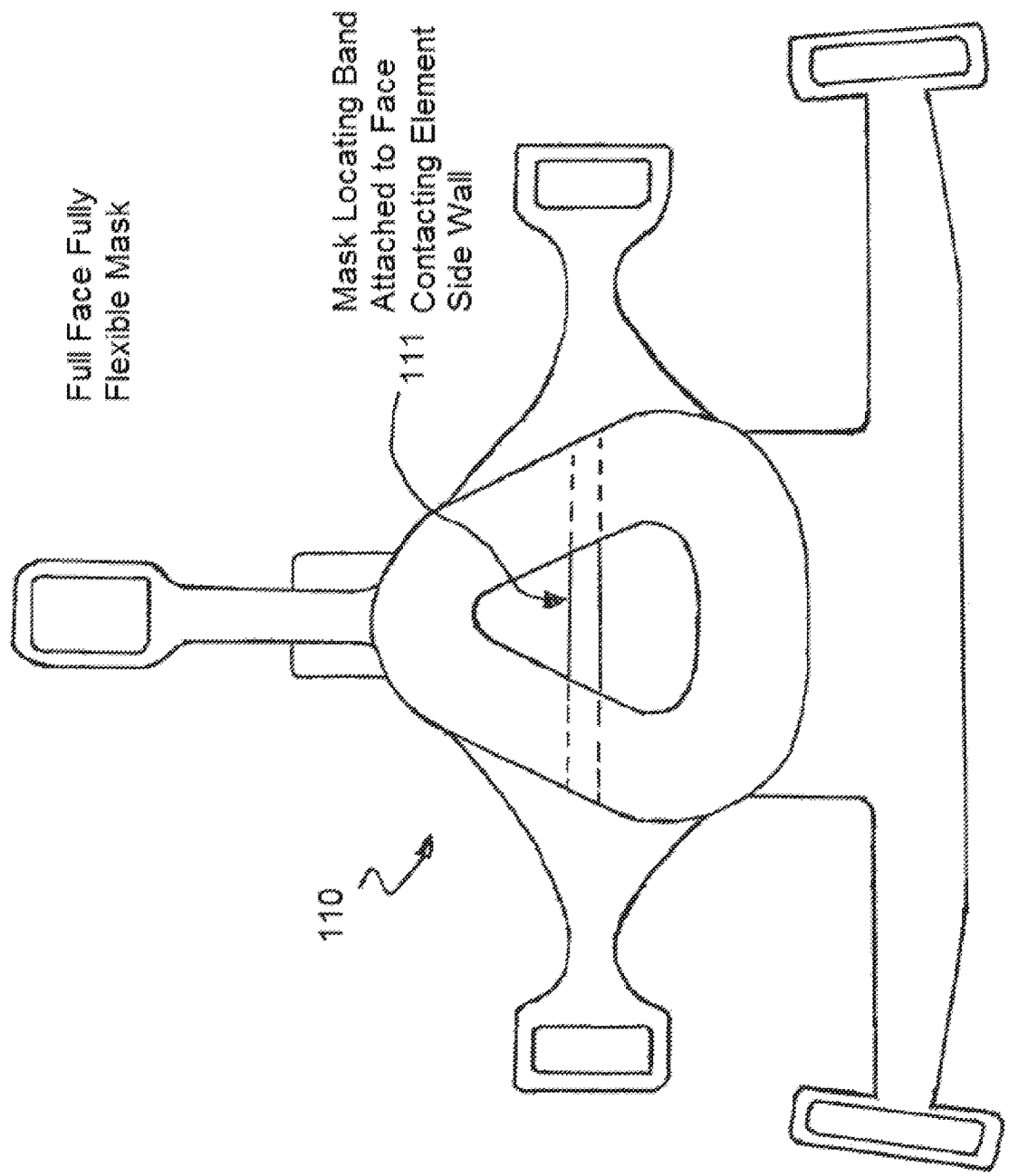
FIG. 20 shows a variant of the mask of FIGS. 18 and 19.

FIG. 20 shows according to an alternative embodiment, a rear (patient side) elevation of a mask 100 including a face contacting part 101 and straps 102 and 103 which comprise the webs 104 and 105 of the shape forming elements of the straps 102 and 103. Mask 100 further comprises an auxiliary fixation arrangement 106 including auxiliary straps 107 and 108.

Auxiliary fixation arrangement 106 pulls mask 100 towards the patients chin. In this embodiment the side straps 107 and 108 also cover a significant portion of the patients cheeks (not shown) thereby reducing the ability of the cheeks to balloon and leak due to a break in the seal allowing escape of internally delivered gas.

Figure 21:
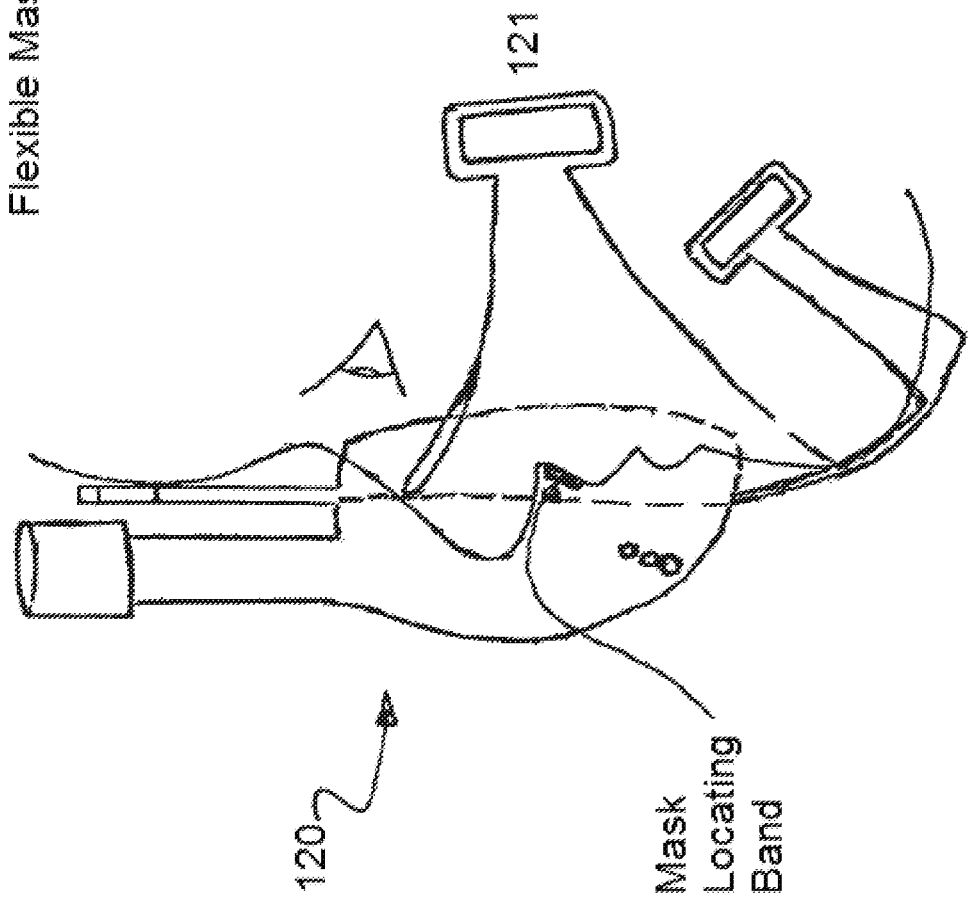
FIG. 21 is a side view of the mask of FIG. 20.

FIG. 21 shows another embodiment of a full face flexible mask 110 which also has a flexible locating band 111 attached to the side wall of the face contacting element. When the mask is placed on the patients face this band 111 locates and sits on the patient's upper lip between their nose and mouth. The band 111 helps to locate and hold the mask 110 in place as the patients jaw opens and moves relative to their nose. Other preferred versions may incorporate similar shape forming element, strap, face contacting element, gas tubing delivery connector and other design features as outlined in FIGS. 2 to 17*b* for the nose only version of the flexible mask. In each case the full face design also incorporates a portion of the shape forming element and related straps designed to provide tension on the flexible mask in the general direction of the chin as shown in FIGS. 20, 21 and 22.

Figure 22:
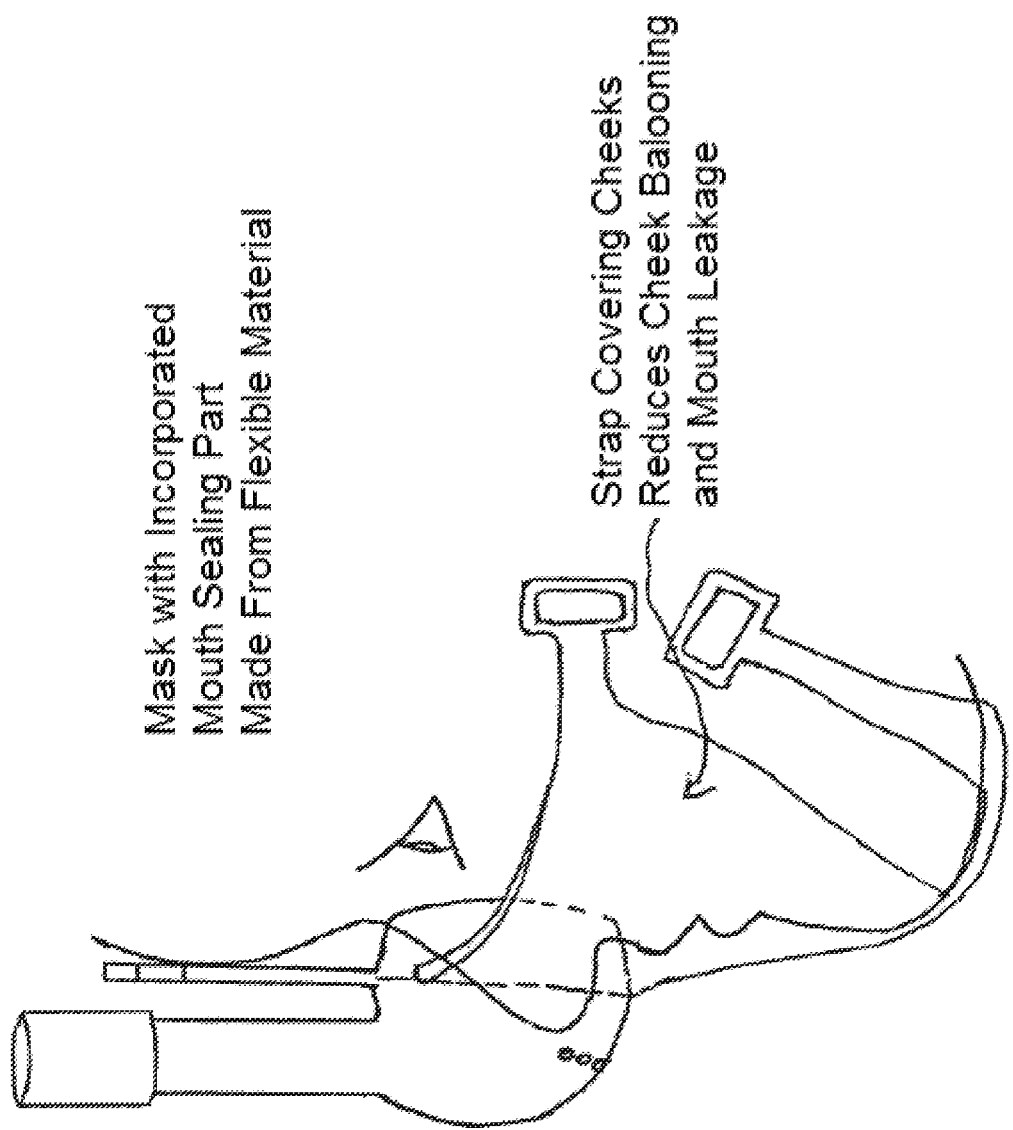
FIG. 22 shows a further embodiment of a full-face mask.

FIG. 22 shows an alternative embodiment of a mask 120 for covering a patient's nose and mouth in order to prevent mouth leakage. In contrast to the conventional more rigid full face masks the mask 120 can conform to the changing facial contours as the mouth moves. In this mask, gas pressure is delivered to the nose only, while the structure covering the patient's mouth acts to prevent air leakage from the mouth. In this embodiment of the full face flexible mask, the side straps 121 cover the patient's cheeks thereby reducing the patient's ability to inflate or balloon their cheeks leading to gas leakage.

In each embodiment shown, the mask effectively 'floats' on the flexible membrane such that the manifold is capable of X or Y axis movement relative to the face engaging membrane. This allows movement in the mask and specifically in the manifold when under loads in either the X-Y or Z directions, allowing the membrane to deform or displace in a rolling motion to retain a gas seal on the face of a wearer. The larger contact length between the web and the manifold walls have numerous advantages. For example, in a case where the mask is pressured in a Y direction and tends to lift of the face, the high contact length webs, help the mask to better accommodate the lifting off tendency by significantly enhanced load distribution through the manifold. The increase in contact length imparts advantages under various load geometries applied to the mask. The larger web connection to the walls of the mask causes a resultant force to be applied closer to the mid height region of the mask. This is no with both the full contact web and the point load contact embodiments as a resultant or notional resultant in the case of the point load embodiment will lie at a location generally in the middle third of the height of the manifold so that the load will be more evenly distributed. In other words the resultant loading is optimally applied above a neutral axis of the manifold. On its face this is against conventional wisdom as this places the resultant load at a location which would cause the straps to engage the user's ear. This would normally motivate away from an adjustment in design which places the resultant force in a compromising location and more particularly around the middle third of the manifold. The web feature of the present invention combines the use of flexible straps and an optimal load distribution which allows a user to avoid unwanted ear loading ensuring user comfort but with the improved performance of the mask.

In another embodiment the mask has the strap connection web characteristics described in the various embodiments above but is further characterised in having a manifold which not only 'floats' relative to the face contacting parts but has some degree of relative planar rotation.

Therefore, instead of the face sealing part being formed about and extending from a periphery of the manifold the face sealing part is connected at a narrowing or waist formed between the face contacting part and the manifold. The floating of the manifold relative to the face contacting membrane provides additional degrees of freedom for the manifold to move reducing transmission of manifold loadings to the face contacting part.

In a further embodiment of the mask described herein, one of the side sections of the face contacting part are provided with a thickening in the walls over at least part of the side section. In another embodiment of the mask described herein, both side sections of the face contacting part are provided with a thickening in the walls over at least part of the side sections. The wall thickenings may be abrupt or gradual according to design requirements. The thickening may be effected by layering at the region of increased thickness or by increasing mould thickness/width at the region of the desired increased thickness. Increasing the thickness of the side regions of the face contacting part provides increased stability in the region and specifically introduces into the art the benefits of a high stiffness wall and its inherent resistance to load but retaining the benefits of flexibility of the face contacting material. Since the sealing problems in masks of the type described herein predominantly occur at the bridge of the nose and at the upper lip, and to a lesser extent lateral of the nose, the stiffening of the side contacting parts does not comprise the rolling flexibility of the contacting part required to maintain the integrity of the seal. Preferably the thickened portion will have a maximum thickness falling within the range 0.5 mm-2.0.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A mask for supplying gas under pressure to an airway of a wearer, the mask comprising:
    a flexible manifold being made of a flexible material, the manifold including an air inlet connected to an air delivery pipe, the manifold having at least a first side wall and a second side wall, the first side wall and the second side wall are at least partially formed by portions of the manifold, a length of each of the first side wall and the second side wall are defined by a distance between an uppermost part of the mask which locates near a nose bridge of the wearer and a lowermost wall of the mask which locates under a nose of the wearer, the first side wall, the second side wall, and lowermost wall together forming a generally triangular shape;
    a flexible face contacting element defining an orifice to accommodate the nose of the wearer, the flexible face contacting element having a face contacting surface;
    a first connecting strap having a first end, the first end of the first connecting strap is connected to the first side wall of the manifold at a location spaced from the face contacting surface in a Z axis away from the face of the wearer and a second end of the first connecting strap connectable to a mask retaining strap;
    a second connecting strap having a first end, the first end of the second connecting strap is connected to the second side wall of the manifold at a location spaced from the face contacting surface in the Z axis and a second end of the first connecting strap connectable to the mask retaining strap;
    wherein the first strap and the second strap engage a respective one of the first side wall and the second side wall of the manifold for distributing opposing distortional forces to a substantial portion of the respective one of the first side wall and the second side wall when the mask is in use;
    wherein the connection of the first strap and second strap to the manifold allow forces exerted by the first strap and the second strap to deform the manifold at least along an X axis and a Y axis to create a variety of different orifice shapes, where the X axis is substantially in a direction defined by the first connecting strap and the second connecting strap, and the Y axis is substantially perpendicular with the X axis and the Z axis;
    wherein a central axis of the first connecting strap and a central axis of the second connecting strap pass through a substantially middle portion of the orifice when the mask is in a neutral position when the mask is not in use;
    wherein the first and second straps respectively engage the respective one of the first side wall and the second side wall of the manifold along each of the first side wall and the second side wall along a portion defining a connecting length, wherein the connecting length is within a range of between 50% and 100% of an extent of a full length of each of the first side wall and the second side wall, thereby joining the first strap and second strap to the respective one of the first side wall and the second side wall of the manifold so that an axis normal to the Y axis intersects with at least part of each strap, a ratio of a height of the manifold to the connecting length of the first strap and the second strap falling within a range of between 0.8 and 2.0;
    wherein the face contacting element includes a flexible membrane configured and arranged to be disposed between a face of the wearer and the manifold, the flexible membrane configured to allow X and Y axis movement of the mask and movement of the mask along the Z axis between the face of the wearer and the manifold;

wherein the flexible membrane deforms or displaces in a rolling motion which retains a gas seal against the face of the wearer; and wherein at least one of the first side wall and the second side wall of the manifold distribute distortional forces from the first connecting strap and the second connecting strap to the manifold, enabling the flexible face contacting element to create a variety of different mask orifice shapes and attitudes.

2. A mask according to claim 1 wherein the first end of the first strap connects to a side wall of the mask via first webs integral with the first side wall of the manifold and the first end of the second strap connects to a side wall of the mask via second webs integral with the second side wall of the manifold and when transmitting a distributed load to the mask, the first webs and the second webs are capable of inducing distortion in the mask along the X, Y and Z axes while the flexible membrane maintains the gas seal between the mask and the face of the wearer.

3. A mask according to claim 2 wherein the connecting length of the first webs and the second webs is greater than a width of the first strap and the second strap.

4. A mask according to claim 3 wherein the first webs and the second webs are integral with the side walls of the manifold and each of the webs contacts a respective manifold side wall at an interface between the manifold and the flexible membrane.

5. A mask according to claim 4 wherein the manifold has an average wall thickness within a range of from 1 mm to 2.5 mm.

6. A mask according to claim 5 wherein the flexible face contacting element has as average wall thickness within a range of from 0.3 mm to 0.7 mm.

7. A mask according to claim 6 wherein the height of the manifold is measured from a lowermost wall of the manifold to an uppermost portion of the manifold at a point which is engageable with the nose bridge of the wearer.

8. A mask according to claim 7 wherein the manifold includes a third strap for anchoring the mask.

9. A mask according to claim 8 wherein the angle of attachment between the first webs and the manifold is an oblique angle and the angle of attachment between the second webs and the manifold is an oblique angle.

10. A mask according to claim 8 wherein the first webs are integral with the first side walls of the manifold and the second webs are integral with the second sidewalls of the manifold, and when transmitting a load to the mask, the first webs and the second webs are capable of inducing distortion in the mask along the X, Y and Z axes while the gas seal is maintained between the mask and the face of the wearer.

11. A mask according to claim 8 wherein the first webs and the second webs each have an oblique angled edge, and wherein the side walls of the manifold have an oblique angled edge.

12. A mask according to claim 11 wherein the first connecting strap and the second connecting strap engage the manifold at a location generally in the middle third of a height of the manifold.

13. A mask according to claim 12 wherein the flexible membrane is configured and arranged to maintain the gas seal between the mask and the face of the wearer irrespective of induced movement of the mask in either the X, Y or Z directions, when a load is applied by the first strap and the second strap on the mask.

14. A mask according to claim 13 wherein, the face contacting element includes at least one part which is thicker than a thickness of remaining parts of the face contacting element.

15. A mask according to claim 14 wherein the face contacting element includes wall thickenings in regions located on sides of the nose of the wearer when the mask is worn by the wearer.

16. A mask according to claim 15 wherein the face contacting element includes a wall thickening in a region located under the nose of the wearer when the mask is worn by the wearer.

17. A mask according to claim 16 wherein the manifold includes external strengthening ribs.

18. A mask according to claim 17 wherein the air inlet is configured to deliver gas to the mask.

19. A mask according to claim 18 wherein the mask includes an auxiliary fixation arrangement configured to apply a pressure to cheeks of the face of the wearer to keep the cheeks retained inwardly and to apply a pressure to a chin of the wearer to maintain an upward force on the chin.

20. A mask according to claim 19 wherein the mask is a full face mask which is configured to cover and seal the nose and mouth of the wearer.

21. A mask according to claim 20 wherein a groove is formed between the face contacting element and the manifold.

22. A mask according to claim 21 wherein the groove allows distortion and displacement of the face contacting element relative to the manifold.

23. A mask according to claim 19 wherein the mask covers and seals only the nose of the wearer.

24. A mask according to claim 23 wherein a groove is formed between the face contacting element and the manifold.

25. A mask according to claim 24 wherein the groove allows distortion and displacement of the face contacting element relative to the manifold.

26. A mask for supplying gas under pressure to an airway of a wearer, the mask comprising:
- a flexible manifold shell made of a flexible material, the manifold shell including means for connection to a gas delivery pipe, the manifold shell having two separate side walls which are at least partially formed by portions of the manifold shell, a length of each side wall defined by a distance between an uppermost part of the mask which locates near a nose bridge of the wearer and a lowermost wall of the mask which locates under a nose of the wearer, the side walls and lowermost wall together forming a generally triangular shape;
- a flexible face contacting element defining an orifice configured and arranged to accommodate a nose of the wearer, the flexible face contacting element having a face contacting surface;
- a first mask shape forming element that defines a first connecting length and configured and arranged to distribute distortional forces to a substantial portion of a first side wall of the at least two side walls, the first mask shape forming element being attached to and integral with a significant portion of the first side wall of the manifold shell along the first side wall which is within a range of between 50%-100% of an extent of a full length of the first side wall and which is spaced from the face contacting surface in a Z axis away from the face of the wearer; and a second mask shape forming element that defines a second connecting length and configured and arranged to distribute distortional forces to a substantial portion of second side wall of the at least two side walls, the second mask shape forming element being attached to and integral with a significant portion of the second side wall of the manifold shell along the second side wall which is within a range of between 50%-100% of an extent of a full length of the second side wall and which is spaced from the face contacting surface in the Z axis away from the face of the wearer, each of the first mask shape forming element and the second mask shape forming element comprising generally triangular shaped webs, one side of each of the generally triangular shaped webs engaging one of the at least two side walls and being one of connected to and connectable to, a strap; and wherein forces exerted by the first mask shape forming element and the second mask shape forming element are capable of deforming the flexible face contacting element and the manifold shell to create a variety of different orifice shapes;

wherein the manifold shell defines a manifold height extending along a Y axis, where the Y axis is substantially perpendicular with the Z axis;

wherein a central axis of the first connecting length and a central axis of the second connecting length pass through a substantially middle portion of the orifice when the mask is in a neutral position when the mask is not in use;

wherein a ratio of the manifold height to each of the first connecting length and the second connecting length falls within a range of from 0.8 to 2.0; and wherein a resultant force applied from a distribution of load through each of the webs over one of predetermined lengths of each of the webs and over a span of point loads applied to each of the webs lies approximately in a middle third of the manifold height to allow the mask to accommodate distortion from such applied load.

27. A mask according to claim 26 wherein the mask is made from a flexible material and the face contacting element includes at least one side provided with a thickening in a wall over at least part of the at least one side of the face contacting element.

28. A mask according to claim 27 wherein the thickening in the wall is one of abrupt and gradual.

29. A mask according to claim 26 wherein the first connecting length joins the first mask shape forming element to the first side wall and the second connecting length joins the second mask shape forming element to the second side wall.

* * * * *